(12) United States Patent
Ben-Bassat et al.

(10) Patent No.: US 7,378,261 B2
(45) Date of Patent: May 27, 2008

(54) METHOD FOR PREPARING PARA-HYDROXYSTYRENE BY BIOCATALYTIC DECARBOXYLATION OF PARA-HYDROXYCINNAMIC ACID IN A BIPHASIC REACTION MEDIUM

(75) Inventors: Arie Ben-Bassat, Newark, DE (US); Sharon L. Haynie, Philadelphis, PA (US); David J. Lowe, Wilmington, DE (US); Lisa L. Huang, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 362 days.

(21) Appl. No.: 10/824,581

(22) Filed: Apr. 14, 2004

(65) Prior Publication Data
US 2004/0248267 A1 Dec. 9, 2004

Related U.S. Application Data

(60) Provisional application No. 60/547,170, filed on Feb. 24, 2004, provisional application No. 60/462,827, filed on Apr. 14, 2003.

(51) Int. Cl.
- C12P 7/22 (2006.01)
- C12N 9/88 (2006.01)
- C12N 5/10 (2006.01)
- C12N 1/21 (2006.01)
- C12N 15/00 (2006.01)
- C12N 11/00 (2006.01)
- C12P 21/06 (2006.01)

(52) U.S. Cl. ............ 435/156; 435/232; 435/69.1; 435/410; 435/320.1; 435/252.32; 435/252.33; 435/252.34; 435/252.35; 435/252.3; 435/325; 435/174

(58) Field of Classification Search ............... 435/156, 435/232, 69.1, 410, 423–429, 252.3, 252.31, 435/252.32, 254.11, 254.2, 257.2, 320.1, 435/252.33, 174, 252.34, 252.35, 325
See application file for complete search history.

(56) References Cited

U.S. PATENT DOCUMENTS

| | | | |
|---|---|---|---|
| 4,503,271 | A | 3/1985 | Fujiwara et al. |
| 5,523,378 | A | 6/1996 | Sounik et al. |
| 5,955,137 | A | 9/1999 | Ago et al. |
| 6,821,730 | B2 | 11/2004 | Hannah |
| 2004/0018600 | A1 | 1/2004 | Ben-Bassat et al. |
| 2005/0019791 | A1 | 1/2005 | Jung et al. |
| 2005/0053966 | A1 | 3/2005 | Poponin |
| 2005/0164211 | A1 | 7/2005 | Hannah |
| 2005/0181409 | A1 | 8/2005 | Park et al. |

FOREIGN PATENT DOCUMENTS

JP 11187870 7/1999

OTHER PUBLICATIONS

Cavin et al., Applied and Environmental Microbiology 64(4):1466-1471, 1998.*
U.S. Appl. No. 60/462,827.
Bruce et al., Solvent Selection Strategies for Extractive Biocatalysis, Biotechnol. Prog. 7: 116-124, 1991.
Lee et al., Decarboxylation of ferulic acid to 4-vinylguaiacol by *Bacillus pumilus* in aqueous-organic solvent two-phase systems, Enzyme Microb. Technol. 23: pp. 261-266, 1998.

* cited by examiner

*Primary Examiner*—Delia M Ramirez

(57) ABSTRACT

A biocatalytic method for preparing para-hydroxystyrene from para-hydroxycinnamic acid is described. The method uses an enzyme source having para-hydroxycinnamic acid decarboxylase activity to catalyze the decarboxylation of para-hydroxycinnamic acid in a biphasic reaction medium to produce para-hydroxystyrene, which is extracted into the organic phase of the biphasic reaction medium. The method results in a high yield of para-hydroxystyrene due to the decreased exposure of the enzyme source to the inhibitory product. The product is readily recovered from the extractant, or may be chemically derivatized directly in the extractant before recovery.

18 Claims, No Drawings

METHOD FOR PREPARING PARA-HYDROXYSTYRENE BY BIOCATALYTIC DECARBOXYLATION OF PARA-HYDROXYCINNAMIC ACID IN A BIPHASIC REACTION MEDIUM

This application claims the benefit of U.S. provisional applications 60/462,827, filed Apr. 14, 2003 and 60/547,170 filed Feb. 24, 2004, the disclosures of which are incorporated in their entirety by reference.

FIELD OF THE INVENTION

The invention relates to the field of molecular biology and microbiology. More specifically, the invention relates to a method for producing para-hydroxystyrene from para-hydroxycinnamic acid using an enzyme source having para-hydroxycinnamic acid decarboxylase activity in a biphasic reaction medium.

BACKGROUND OF THE INVENTION

Para-hydroxystyrene (pHS) is an aromatic compound that has potential utility in a wide variety of industrial applications. For example, pHS and its acetylated derivative, para-acetoxystyrene (pAS) have application as monomers for the production of resins, elastomers, adhesives, coatings, automotive finishes, inks and electronic materials, and additives in elastomer and resin formulations.

A number of methods for the chemical synthesis of pHS are known. For example, pHS may be produced from ethyl benzene in a five-step process (U.S. Pat. No. 4,503,271) or from para-hydroxyacetophenol in a two step process (U.S. Pat. No. 5,523,378). Although it is possible to generate pHS by these methods, they typically require strongly acidic or basic reaction conditions, high reaction temperature, and generate large amounts of unwanted byproducts. In addition, chemical methods require expensive starting materials, which raise the cost of producing pHS. Despite the wide variety of uses for pHS, an inexpensive source of the material has not been developed.

A biological process for the production of pHS from a simple carbon source such as glucose is described by Ben-Bassat et al. (U.S. Patent Application Publication No. 2004/0018600). In that disclosure, a recombinant host cell expressing at least one gene encoding a polypeptide having para-hydroxycinnamic acid decarboxylase (PDC) activity in combination with either at least one gene encoding a polypeptide having tyrosine ammonia lyase (TAL) activity or at least one gene encoding a polypeptide having phenylalanine ammonia lyase (PAL) activity is used to produce pHS. A PAL activity converts phenylalanine to para-hydroxycinnamic acid (PHCA) in the presence of a P-450/P-450 reductase [cinnamate-4-hydroxylase (C4H) and P-450 reductase] system. An enzyme having a high TAL activity converts tyrosine directly to pHCA without any intermediate steps. Then, para-hydroxycinnamic acid decarboxylase (PDC) converts the pHCA to pHS. However, a problem encountered with the biological production of pHS is end-product inhibition, which limits product yield. Specifically, the rate of production of the product by the microorganism decreases as the concentration of the product increases. Additionally, the PDC enzyme and the microorganism are inactivated by the product when a certain critical concentration is reached in the fermentation medium.

One approach to mitigate end-product inhibition by pHS is to use two-phase extractive fermentation, in which the pHS produced by a recombinant production host is extracted into an immiscible organic phase during the fermentation so that it never reaches an inhibitory or critical concentration, as described by Ben Bassat et al. in co pending U.S. Patent Application No. 60/462,827. The methods described in that disclosure resulted in improved yields for pHS. However, still higher yields are required for commercial applications.

Tetsuji et al. (JP 11187870) describe a method for producing pHS, having a deuterium atom at the vinyl position, from pHCA using PDC isolated from *Klebsiella oxytoca*. The decarboxylase reaction is carried out in an aqueous buffer containing deuterated water. Ago et al. in U.S. Pat. No. 5,955,137 describe a method for producing 4-vinylguaiacol (4-hydroxy-3-methoxystyrene), a derivative of pHS, from ferulic acid (4-hydroxy-3-methoxycinnamic acid) in aqueous buffer using an enzyme source having ferulic acid decarboxylase activity. The product yields in both these methods are limited by product inhibition of the enzyme. Additionally, the recovery of the product is complicated because the product must be isolated from the substrate, biocatalyst, and buffer salts.

A biocatalytic method for producing pHS from PHCA in a biphasic reaction medium would decouple the production of PHCA and pHS, thereby enabling the optimization of both processes independently. The use of a biphasic reaction medium, consisting of an aqueous phase and a water-immiscible organic phase, in biocatalytic reactions can provide both kinetic and thermodynamic advantages (Bruce et al., *Biotechnol. Prog.* 7:116-124 (1991)). With the proper choice of organic solvent, the product is continuously removed from the aqueous phase, thereby reducing product inhibition, resulting in higher product yields. Moreover, product recovery is greatly simplified because the product can be readily isolated from the organic phase. Lee et al. (*Enzyme Microb. Technol.* 23:261-266 (1998)) describe the production of 4-vinylguaiacol (4-hydroxy-3-methoxystyrene), a derivative of pHS, via the decarboxylation of ferulic acid by resting cells of *Bacillus pumilus* having ferulic acid decarboxylase activity using a two-phase, biocatalytic process. Several solvents were evaluated, including chloroform, methylene chloride, ethylacetate, ethyl ether, petroleum ether, cyclohexane, and C5-C8 alkanes. Hexane was selected as the preferred solvent. However, the production of pHS from pHCA using an enzyme source having PDC activity in a biphasic reaction medium is not described in that disclosure.

Therefore, the need exists for a method for producing pHS in high yield. The need also exists for a biocatalytic method for producing pHS in which the activity of the biocatalyst is preserved. It is also desirable to be able to reuse the biocatalyst over multiple reaction cycles for the method to be commercially viable.

Applicants have solved the stated problem by discovering a method for producing pHS in high yield using biocatalytic conversion of pHCA to pHS using an enzyme source having para-hydroxycinnamic acid decarboxylase activity in a biphasic reaction medium.

SUMMARY OF THE INVENTION

The present invention provides methods for producing para-hydroxystyrene by biocatalytic decarboxylation of para-hydroxycinnamic acid in a biphasic reaction medium. In one embodiment, the invention provides a process for producing para-hydroxystyrene comprising:

a) providing an enzyme source having para-hydroxycinnamic acid decarboxylase activity, said enzyme source comprising a polypeptide having the amino acid sequence as set forth in SEQ ID NO:2 or SEQ ID NO:4;

b) contacting said enzyme source with para-hydroxycinnamic acid in a biphasic reaction medium comprising an aqueous phase and an extractant, said extractant being a water-immiscible organic solvent selected from the group consisting of toluene, methyl decanoate, 2-undecanone, dichloromethane, hexane, 2-decanol, 4-decanol, 3-decanone, 4-decanone, 1-nonanol, 2-nonanol, 2-heptanol and mixtures thereof, to form para-hydroxystyrene which is extracted into the extractant of the biphasic reaction medium;

c) separating the extractant from the aqueous phase; and d) optionally, recovering the para-hydroxstyrene from the extractant.

In another embodiment, the invention provides a process for producing para-hydroxystyrene comprising:

a) providing a production host which produces para-hydroxycinnamic acid;

b) growing the production host in a fermentation medium wherein the production host produces para-hydroxycinnamic acid into the fermentation medium;

c) contacting the fermentation medium from step (b) with an enzyme source having para-hydroxycinnamic acid decarboxylase activity, said enzyme source comprising a polypeptide having the amino acid sequence as set forth in SEQ ID NO:2 or SEQ ID NO:4, in a biphasic reaction medium comprising the fermentation medium and an extractant, said extractant being a water-immiscible organic solvent selected from the group consisting of toluene, methyl decanoate, 2-undecanone, dichloromethane, hexane, 2-decanol, 4-decanol, 3-decanone, 4-decanone, 1-nonanol, 2-nonanol, 2-heptanol and mixtures thereof, to form para-hydroxystyrene, which is extracted into the extractant of the biphasic reaction medium;

d) separating the extractant from the fermentation medium; and e) optionally recovering the para-hydroxystyrene from the extractant.

SEQUENCE DESCRIPTIONS

The invention can be more fully understood from the following detailed description and the accompanying sequence descriptions, which form a part of this application.

The following sequences conform with 37 C.F.R. 1.821-1.825 ("Requirements for patent applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37C.F.R. §1.822.

SEQ ID NO:1 is the nucleotide sequence of the para-hydroxycinnamic acid decarboxylase gene (pdc1) from *Lactobacillus plantarum*.

SEQ ID NO:2 is the amino acid sequence of para-hydroxycinnamic acid decarboxylase (PDC1) from *Lactobacillus plantarum*.

SEQ ID NO:3 is the nucleotide sequence of the para-hydroxycinnamic acid decarboxylase gene (pdc2) from *Bacillus subtilis*.

SEQ ID NO:4 is the amino acid sequence of para-hydroxycinnamic acid decarboxylase (PDC2) from *Bacillus subtilis*.

SEQ ID NOs:5-8 are the nucleotide sequences of primers used to amplify pdc genes, as described in Example 1.

SEQ ID NOs:9-12 are the nucleotide sequences of primers used to construct *E. coli* strain WS158, as described in Example 6.

SEQ ID NOs:13 and 14 are the nucleotide sequences of primers used to confirm the successful construction of *E. coli* strain WS158, as described in Example 6.

DETAILED DESCRIPTION OF THE INVENTION

The invention provides a method for the production of para-hydroxystyrene (pHS) from para-hydroxycinnamic acid (PHCA) using an enzyme source having para-hydroxycinnamic acid decarboxylase (PDC) activity in a biphasic reaction medium. The method results in high product yields of pHS due to the decreased exposure of the enzyme source to the inhibitory product, which is extracted into the organic phase of the biphasic reaction medium. Moreover, the method provides excellent preservation of enzymatic activity and reuse of the enzyme source for many reaction cycles. The method is useful because pHS and its acetylated derivative, para-acetoxystyrene have application as monomers for the production of resins, elastomers, adhesives, coatings, automotive finishes, inks and electronic materials, and additives in elastomer and resin formulations.

The following definitions are used herein and should be referred to for interpretation of the claims and the specification.

"CA" is the abbreviation used for cinnamic acid.

"pHCA" is the abbreviation used for para-hydroxycinnamic acid, also known as para-hydroxycinnamate or p-coumaric acid.

"pHS" is the abbreviation used for para-hydroxystyrene, also known as 4-vinylphenol.

"PDC" is the abbreviation used for PHCA decarboxylase.

"PDC1" is the abbreviation used for the pHCA decarboxylase from *Lactobacillus plantarum*.

"PDC2" is the abbreviation used for the pHCA decarboxylase from *Bacillus subtilis*.

"pdc" is the abbreviation for a gene that encodes an enzyme with PDC activity.

"pdc1" is the abbreviation for the pdc gene from *Lactobacillus plantarum*.

"pdc2" is the abbreviation for the pdc gene from *Bacillus subtilis*.

"TAL" is the abbreviation used for tyrosine ammonia lyase.

"PAL" is the abbreviation used for phenylalanine ammonia lyase.

"PAH" is the abbreviation used for phenylalanine hydroxylase.

The term "TAL activity" refers to the ability of a protein to catalyze the direct conversion of tyrosine to PHCA.

The term "PAL activity" refers to the ability of a protein to catalyze the conversion of phenylalanine to cinnamic acid.

"pal" represents a gene that encodes an enzyme with PAL activity.

"tal" represents a gene that encodes an enzyme with TAL activity.

The term "PAL/TAL activity" or "PAL/TAL enzyme" refers to a protein, which contains both PAL and TAL activity. Such protein has at least some specificity for both tyrosine and phenylalanine as an enzymatic substrate.

The term "P450/P450 reductase system" refers to a protein system responsible for the catalytic conversion of cinnamic acid to PHCA. The P450/P450 reductase system is one of several enzymes or enzyme systems known in the art that performs a cinnamate 4-hydroxylase function. As used herein the term "cinnamate 4-hydroxylase" will refer to the general enzymatic activity that results in the conversion of cinnamic acid to pHCA, whereas the term "P-450/P450 reductase system" will refer to a specific binary protein system that has cinnamate 4-hydroxylase activity.

The term "biphasic reaction medium" refers to a medium comprising an aqueous phase and a suitable amount of an extractant.

The term "aqueous phase" refers to an aqueous solution including but not limited to an aqueous buffer, a non-buffered aqueous solution, a fermentation medium, or a fermentation supernatant.

The term "extractant" refers to a solvent into which pHS may be dissolved. Typical extractants of the invention are water-immiscible organic solvents.

The term "organic phase" refers to the organic solvent that serves as the extractant in the biphasic reaction medium.

The terms "growth medium", and "fermentation medium" are herein used interchangeably to refer to an aqueous solution containing nutrients for culturing microorganisms. The growth medium may additionally contain the microorganism, the product produced by the microorganism, metabolic intermediates, and other components such as salts, vitamins, amino acids, cofactors, and antibiotics.

The term "fermentation supernatant" refers to the fermentation medium after the fermentation is completed, wherein the production host and insoluble products are removed by methods known in the art, including, but not limited to centrifugation or filtration.

The term "partition coefficient" refers to the equilibrium constant for the extraction of the product into the organic solvent, specifically $K=[Product]_{Org}/[Product]_{Aq}$.

The "log value" of a solvent refers to the logarithm of the solvent's partition coefficient in a standard octanol:water mixture. The log P value provides a quantitative measure of the polarity of the solvent.

The term "fermentable carbon substrate" refers to a carbon source capable of being metabolized by host organisms of the present invention and particularly carbon sources selected from the group consisting of monosaccharides, oligosaccharides, polysaccharides, one-carbon substrates and/or mixtures thereof.

"Nucleic acid" refers to a molecule, which can be single stranded or double stranded, composed of monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

The invention encompasses more than the specific exemplary sequences because it is well known in the art that alterations in a gene, which result in the production of a chemically equivalent amino acid at a given site, but do not effect the functional properties of the encoded protein, are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

"Gene" refers to a nucleic acid fragment that expresses a specific protein. As used herein, the gene may or may not include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" host cells.

"Wildtype host cell" or "native host cell" refers to a host organism that is the original or natural version of the organism, i.e., an organism that has not been transformed.

The term "enzyme source" refers to a source having PDC activity including, but not limited to the purified or partially purified enzyme itself, wildtype or recombinant host cells having the enzyme activity, cell-free extract obtained from such cells by means known in the art, and treated wildtype or recombinant host cells having the enzyme activity.

The terms "treated wildtype host cells" and "treated recombinant host cells" refer to wild type host cells and recombinant host cells, respectively, that have been treated by means including, but not limited to, washing, lyophilizing, treating with acetone, or permeabilizing with surfactants, such as Cetyltrimethylammonium bromide (CTAB) and Triton X-100; solvents, such as toluene, chloroform, dimethylformamide (DMF) and dimethyl sulfoxide (DMSO); and antibiotics.

The term "biocatalyst" refers to an enzyme source having the required activity to catalyze a particular reaction. In the present invention the term "biocatalyst" refers to an enzyme source having pHCA decarboxylase activity.

The term "biocatalytic reaction" refers to a reaction that is catalyzed by an enzyme source. In the present invention the term "biocatalytic reaction" refers to the decarboxylation of pHCA to give pHS, which is catalyzed by an enzyme source having PHCA decarboxylase activity.

The term "expression" as used herein is intended to mean the transcription and translation to gene product from a gene coding for the sequence of the gene product. In the expression, a DNA chain coding for the sequence of gene product is first transcribed to a complementary RNA which is often a messenger RNA and, then, the thus transcribed messenger RNA is translated into the above-mentioned gene product if the gene product is a protein.

"Overexpressing strain" or "overproducing strain" refers to a recombinant microorganism that produces a gene product at a level that exceeds the level of production in wildtype or non-transformed microorganisms.

The term "production host" as used herein, refers to a microorganism having the ability to produce pHCA for use in the method of the present invention. As defined herein the production host may be a wildtype or recombinant host cell.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

"PCR" or "polymerase chain reaction" is a technique used for the amplification of specific DNA segments (U.S. Pat. Nos. 4,683,195 and 4,800,159).

All ranges given herein include the end of the ranges and also all the intermediate range points.

Standard recombinant DNA and molecular cloning techniques used herein are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The instant invention provides a method for producing para-hydroxystyrene (pHS) from para-hydroxycinnamic acid (PHCA) using an enzyme source having para-hydroxycinnamic acid decarboxylase (PDC) activity in a biphasic reaction medium. The pHS produced, which is inhibitory toward the PDC enzyme, is extracted into the organic phase of the biphasic reaction medium, thereby maintaining a very low concentration in the aqueous phase. The pHS is readily recovered from the extractant or can be chemically derivatized in the extractant before recovery.

Sources of pHCA

The starting material for the method of the instant invention, i.e., the PHCA substrate, may be obtained in a number of ways. For example, pHCA, predominantly in the trans form, is available commercially from companies such as Aldrich (Milwaukee, Wis.) and TCI America (Portland, Oreg.). Additionally, PHCA may be prepared by chemical synthesis using any method known in the art. For example, pHCA may be obtained by reacting malonic acid with para-hydroxybenzaldehyde as described by Piftet et al. in U.S. Pat. No. 4,316,995, or by Alexandratos in U.S. Pat. No. 5,990,336. Alternatively, pHCA may also be isolated from plants (R. Benrief et al. *Phytochemistry* 47:825-832 (1998) and U.S. Patent Application Publication No. 2002/0187207). In one embodiment, the source of pHCA is from bioproduction using a production host. In another embodiment, the production host is a recombinant host cell, which may be prepared using standard DNA techniques. These recombinant DNA techniques are described by Sambrook, J., Fritsch, E. F. and Maniatis, T. *Molecular Cloning: A Laboratory Manual*, Second Edition, Cold Spring Harbor Laboratory Press, Cold Spring Harbor, N.Y. (1989), incorporated herein by reference.

Suitable production hosts for the production of pHCA include, but are not limited to *Escherichia, Methylosinus, Methylomonas, Pseudomonas, Streptomyces, Corynebacterium*, and *Rhodobacter*. In one embodiment, the host cell for the production of pHCA is *Escherichia coli* or *Pseudomonas putida*. In another embodiment, the host cells for the production of PHCA are mutant strains of these bacteria that overproduce either phenylalanine or tyrosine. Tyrosine overproducing strains are used when the production of pHCA is carried out via a pathway that involves tyrosine, while phenylalanine overproducing strains are used when PHCA is produced via a pathway that involves phenylalanine, as described infra. Tyrosine overproducing strains of *Escherichia* and *Pseudomonas*, as well as other bacteria, are known in the art (Maiti et al., *Antibiotic Bulletin* 37:51-65 (1995)). An example of an *Escherichia* tyrosine overproducing strain that may be used is *E. coli* TY1, available from OmniGene Bioproducts, Inc. Cambridge, Mass. Phenylalanine overproducing strains of *Escherichia* and *Pseudomonas*, as well as other bacteria, are also known in the art (Maiti et al, supra and Bongaertes et al., *Metabolic Engineering* 3:289-300 (2001)). An example of a phenylalanine overproducing strain that may be used is *E. coli* NST74, available as strain ATCC No. 31884 from the American Type Culture Collection, Manassas, Va.

In one embodiment, PHCA is produced as described by Qi et al. in U.S. Patent Application Publication No. 2003/0079255, incorporated herein by reference. According to that disclosure, pHCA may be produced using a recombinant microorganism engineered to express at least one gene encoding a phenylalanine hydroxylase (PAH) activity and at least one gene encoding a tyrosine ammonia lyase (TAL) activity. This transformed microorganism metabolizes a fermentable carbon source, such as glucose, to phenylalanine, which is converted to tyrosine by PAH. The tyrosine produced is converted to PHCA by the TAL enzyme. Any suitable enzyme possessing a TAL activity may be used. For example, an enzyme having both PAL and TAL (PAL/TAL) activity may be used. TAL enzymes, produced through mutagenesis of wild-type yeast PAL enzymes to have enhanced TAL activity, may also be used, as described by Gatenby et al. in U.S. Pat. No. 6,368,837. Alternatively, an inducible TAL enzyme from the yeast *Trichosporon cutaneum*, as described by Breinig et al. (U.S. Patent Application Publication No. 2004/0023357) or a bacterial TAL enzyme such as that described by Kyndt et al. (*FEBS Lett.* 512:240-244 (2002)) or by Huang et al. (co pending U.S. Patent Application No. 60/397,820, WO 2004/009795) may be used.

In another embodiment, para-hydroxycinnamic acid is produced by any one of the methods disclosed by Gatenby et al. supra, incorporated herein by reference. For example, pHCA may be produced using a recombinant microorganism engineered to express a gene encoding a yeast PAL activity and genes encoding a plant P450/P450 reductase system. This transformed microorganism metabolizes a fermentable carbon source, such as glucose, to phenylalanine, which is converted to cinnamic acid (CA) by the PAL enzyme. CA is subsequently converted to pHCA by the action of the P-450/P-450 reductase system. Alternatively, pHCA may be produced using a recombinant microorganism expressing a gene encoding a TAL activity. The TAL enzyme converts tyrosine directly to pHCA. Any suitable TAL enzyme may be used, as described supra.

For the bioproduction of pHCA, the microorganism to be used is cultured in a fermentor in a suitable growth medium. Any suitable fermentor may be used including a stirred tank fermentor, an airlift fermentor, a bubble fermentor, or any combination thereof. Materials and methods for the maintenance and growth of microbial cultures are well known to those in the art of microbiology or fermentation science (See for example, Bailey et al., *Biochemical Engineering Fundamentals*, second edition, McGraw Hill, New York, 1986). Consideration must be given to appropriate growth medium, pH, temperature, and requirements for aerobic, microaerobic, or anaerobic conditions, depending on the specific requirements of the microorganism for the specific gene expression. The growth medium used is not critical, but it must support growth of the microorganism used and promote the enzymatic pathway necessary to produce the desired product. A conventional growth medium may be used, including, but not limited to complex media, containing organic nitrogen sources such as yeast extract or peptone and a fermentable carbon source; minimal media; and defined media. Suitable fermentable carbon sources include, but are not limited to monosaccharides, such as glucose or fructose, disaccharides, such as lactose or sucrose, oligosaccharides and polysaccharides, such as starch or cellulose, one-carbon substrates and/or mixtures thereof. In addition to the appropriate carbon source, the growth medium may contain a suitable nitrogen source, such as an ammonium salt, yeast extract or peptone; minerals, salts, cofactors, buffers and other components, known to those skilled in the art (Bailey et al. supra).

A batch or a fed-batch fermentation may be used. Batch fermentation, which is well known in the art, is a closed system in which the composition of the medium is set at the beginning of the fermentation and is not subjected to artificial alterations during the process. Fed-batch fermentation is a variation of the standard batch system, in which the nutrients, for example glucose, are added in increments during the fermentation. The amount and the rate of addition of the nutrient may be determined by routine experimentation. For example, the concentration of critical nutrients in the fermentation broth may be monitored during the fermentation. Alternatively, more easily measured factors such as pH, dissolved oxygen, and the partial pressure of waste gases, such as carbon dioxide, may be monitored. From these measured parameters, the rate of nutrient addition may be determined.

Enzyme Sources Having PDC Activity

Enzymes having PDC activity may be found in a variety of bacteria including *Klebsiella oxytoca* (Hashidoko et al. *Biosci. Biotechnol. Biochem.* 65:2604-2612 (2001)), *Erwinia uredovora* (Hashidoko et al. *Biosci. Biotechnol. Biochem.* 57:215-219 (1993)), *Lactobacillus* species, such as *Lactobacillus brevis, Lactobacillus crispatus, Lactobacillus fermentum, Lactobacillus paracasei, Lactobacillus pentosus*, and *Lactobacillus plantarum* (Van Beek et al. *Appl. Environ. Microbiol.* 66:5322-5328 (2000)), species of *Enterobacter, Klebsiella* and *Hafnia* (Lindsay et al. *J. Appl. Bact.* 39:181-187 (1975)) and *Bacillus subtilis* (Cavin et al. *Appl. Environ. Microbiol.* 64:1466-1471 (1998)). In one embodiment, the source of PDC enzyme is *Lactobacillus plantarum* (PDC1), having the amino acid sequence as set forth in SEQ ID NO:2. In another embodiment, the source of PDC enzyme is *Bacillus subtilis* (PDC2), having the amino acid sequence as set forth in SEQ ID NO:4.

Useful enzyme sources having PDC activity include the purified or partially purified enzyme itself, wildtype or recombinant host cells having the enzyme activity, and cell-free extract obtained from such cells by means known in the art. In one embodiment, the wildtype cells having PDC activity are *Lactobacillus plantarum* or *Bacillus subtilis*.

In another embodiment, the enzyme source is a recombinant host cell having PDC activity, which may be constructed by transforming a suitable host cell with a gene that encodes a PDC enzyme using methods known in the art (Maniatis, supra). In one embodiment, the pdc gene is isolated from *Lactobacillus plantarum*, given as SEQ ID NO:1. In another embodiment, the pdc gene is isolated from

*Bacillus subtilis*, given as SEQ ID NO:3, is used. The pdc gene and gene product may be produced in heterologous host cells, particularly in the cells of microbial hosts.

Microbial Host Cells as Enzyme Sources

Microbial expression systems and expression vectors containing regulatory sequences that direct high level expression of foreign proteins are well known to those skilled in the art. Any of these could be used to construct chimeric genes for production of the pdc gene. These chimeric genes could then be introduced into appropriate microorganisms via transformation to provide high level expression of the enzyme.

Accordingly, it is expected for example that introduction of a chimeric gene encoding the PDC enzyme under the control of the appropriate promoters will demonstrate increased production of the enzyme. It is contemplated that it will be useful to express the pdc gene both in native host cells as well as heterologous hosts. Introduction of the present gene into the native host will result in elevated levels of existing production of the PDC enzyme. Additionally, the pdc gene may also be introduced into non-native host bacteria.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the recombinant host cell, although it is to be understood that such control regions need not be derived from the genes native to the specific species chosen as a production host.

Initiation control regions or promoters which are useful to drive expression of the pdc gene in the desired host cell are numerous and familiar to those skilled in the art. Virtually any promoter capable of driving this gene is suitable for the present invention including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary; however, it is most preferred if included.

In one embodiment, heterologous host cells for expression of the pdc gene are microbial hosts that can be found broadly within the fungal or bacterial families and which grow over a wide range of temperature, pH values, and solvent tolerances. For example, it is contemplated that any bacteria, yeast, or filamentous fungi will be suitable hosts for expression of the pdc gene. Because transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, and/or saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression.

Examples of suitable host strains include, but are not limited to bacteria, such as the enteric bacteria (Escherichia, and *Salmonella* for example) as well as *Bacillus, Lactobacillus, Acinetobacter, Streptomyces, Methylobacter*, and *Pseudomonas*; Cyanobacteria, such as *Rhodobacter* and *Synechocystis*; yeasts, such as *Saccharomyces, Zygosaccharomyces, Kluyveromyces, Candida, Hansenula, Debaryomyces, Mucor, Pichia* and *Torulopsis*; filamentous fungi such as *Aspergillus* and *Arthrobotrys*; and algae such *Spirulina, Haemotacoccus*, and *Dunalliela*. The pdc gene may be produced in these and other microbial hosts to produce high levels of PDC enzyme for use in the biocatalytic conversion pHCA to pHS. In one embodiment, the host strain is *Escherichia, Pseudomonas,* or *Pichia*. The recombinant microbial cells may be cultured as described above.

Plant Host Cells as Enzyme Sources

In another embodiment, plant cells containing the pdc gene are used. The pdc gene may be used to create transgenic plants having the ability to express the microbial gene for the production of PDC. Preferred plant hosts will be any variety that will support a high production level of PDC. Suitable green plants include, but are not limited to: soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa*, L), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Overexpression of the PDC enzyme may be accomplished by first constructing a chimeric gene of the present invention in which the coding regions are operably linked to promoters capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals must also be provided. The chimeric gene may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequence or the present invention should be capable of promoting expression of the present gene product. High-level plant promoters that may be used in this invention, for example, include the promoter of the small subunit (ss) of the ribulose-1,5-bisphosphate carboxylase from soybean (Berry-Lowe et al., *Journal of Molecular and Applied Genetics*, 1:483-498 1982)), and the promoter of the chlorophyll a/b binding protein. These two promoters are known to be light-induced in plant cells (see, for example, *Genetic Engineering of Plants, an Agricultural Perspective,* A. Cashmore, Plenum, N.Y. (1983), pp. 29-38; Coruzzi, G. et al., *J. Biol. Chem.,* 258:1399 (1983), and Dunsmuir, P. et al., *Journal of Molecular and Applied Genetics,* 2:285 (1983)).

Plasmid vectors comprising the chimeric gene can then be constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus multiple events must be screened in order to obtain lines displaying the desired expression level and pattern. Such screening may be accomplished by Southern analysis of DNA blots (Southern, *J. Mol. Biol.* 98, 503, (1975)), Northern analysis of mRNA expression (Kroczek, *J. Chromatogr. Biomed. Appl.,* 618(1-2) 133-145 (1993)), Western analysis of protein expression, or phenotypic analysis.

For some applications it will be useful to direct the PDC enzyme to different cellular compartments. It is thus envisioned that the chimeric gene described above may be further supplemented by altering the coding sequences to encode enzymes with appropriate intracellular targeting sequences such as transit sequences (Keegstra, K., *Cell* 56:247-253 (1989)), signal sequences or sequences encoding endoplasmic reticulum localization (Chrispeels, J. J., *Ann. Rev. Plant Phys. Plant Mol. Biol.* 42:21-53 (1991)), or nuclear localization signals (Raikhel, N. *Plant Phys.* 100: 1627-1632 (1992)) added and/or with targeting sequences that are already present removed. While the references cited give examples of each of these, the list is not exhaustive and more targeting signals of utility may be discovered in the future that are useful in the invention.

Culturing of plant cells is usually carried out under aerobic conditions, for example, by shaking culture or submerged aeration culture, at a temperature between 15° C. and 40° C. for 1 to 30 days.

Types of Enzyme Sources Having PDC Activity

After the completion of culturing, the wildtype or recombinant host cells may be collected by any known method, e.g., centrifugation or filtration, and then used as the enzyme source of PDC activity in the method of the present invention. Optionally, the cells may be treated by washing, lyophilizing, or treating with acetone prior to use. The cells may also be treated with a permeabilizing agent to make their cell membrane more permeable to organic chemical substances. Suitable permeabilizing agents are well known in the art and include, but are not limited to surfactants, such as Cetyltrimethylammonium bromide (CTAB) and Triton X-100; solvents, such as toluene, chloroform, dimethylformamide (DMF) and dimethyl sulfoxide (DMSO); and antibiotics.

In another embodiment, the PDC enzyme produced intracellularly or extracellularly by the host cells is isolated and purified using methods well known in the art. For example, in the case of an intracellularly produced PDC enzyme, the isolation and purification may be carried out in the following manner. The cells are separated from the culture medium using known methods including, but not limited to centrifugation or filtration. The cells are washed and then disrupted using a French press, an ultrasonic disrupter, a homogenizer, a Dyno Mill, or other means known in the art, to obtain a cell-free extract. The cell-free extract is centrifuged to remove cell debris. In one embodiment, the cell-free extract is used as the enzyme source of PDC enzyme activity.

In another embodiment, the PDC enzyme is purified from the cell-free extract using methods known in the art, including but not limited to ammonium sulfate precipitation, anion exchange chromatography, hydrophobic interaction chromatography, size exclusion chromatography, electrophoresis and the like. When the PDC enzyme is produced extracellularly the culture medium may be treated in the same manner as described for the cell-free extract to obtain the purified enzyme.

In another embodiment, the wildtype or recombinant host cells, the cell-free extract, or the purified enzyme having PDC activity is immobilized before use. Methods of cell and enzyme immobilization are well-know in the art (see for example, Weetal, *Methods in Enzymology,* Vol. XLIV, K. Mosbach, ed., Academic Press, New York (1976), Bickerstaff, *Immobilization of Enzymes and Cells,* Methods in Biotechnology Series, Humana Press, Totowa, N.J. (1997), and Taylor, *Protein Immobilization: Fundamentals and Applications,* BioProcess Technology, vol. 14, Marcel Dekker, New York (1991)). For example, the enzyme source having PDC activity may be immobilized by entrapment in a polymer gel, adsorption onto a solid support, covalent crosslinking using a bifunctional reagent, or covalent binding to an insoluble matrix, such as glass, polystyrene, nylon, or polyacrylic acid derivatives. In one embodiment, a cell-free extract or the purified enzyme is immobilized by covalent attachment to oxirane acrylic beads, available from Sigma Chemical (St. Louis, Mo.). In another embodiment, wildtype or recombinant host cells are immobilized by entrapment in calcium alginate beads, as described by Bickerstaff, supra. Optionally, the entrapped cells may be crosslinked by polyethyleneimine and glutaradehyde or other suitable crosslinking agents known in the art.

Extractants

The selection of useful extractants for the biocatalytic conversion of pHCA to pHS using an enzyme source having PDC activity is important. The extractant preferably should meet the following requirements for use in the method of the present invention: low solubility in water, large partition coefficient for the product pHS, low partition coefficient for the substrate pHCA, high chemical and thermal stability, nonbiodegradability, low cost, available in large quantities, and favorable properties for product recovery. Additionally, the extractant should not inhibit the enzyme activity of the enzyme source and the enzyme source should be stable in the biphasic reaction medium consisting of the aqueous phase and the extractant so that the enzyme may be recovered and reused in multiple conversion cycles. The extractant is typically a water-immiscible organic solvent. Solvent selection strategies for extractive biocatalysis using living cells have been described (Bruce et al. *Biotechnol. Prog.* 7:116-124 (1991)). In that disclosure, biocompatibility of the solvent is predicted based on its log P value, which is the logarithm of the solvent's partition coefficient in a standard octanol:water mixture. The log P value provides a quantitative measure of the polarity of the solvent. However, no correlation between the log P value of the solvent and its biocompatibility with the enzyme source of PDC activity used herein was found. The biocompatibility of solvents for use in the method of the present invention must be determined empirically by exposing the enzyme source having PDC activity to the organic solvent and measuring the activity of the PDC enzyme after exposure. In these experiments, care should be taken to ensure that the solvents do not contain any impurities that might be inhibitory. Suitable solvents include, but are not limited to toluene (CAS No. 108-88-3, log P=2.8), methyl decanoate (CAS No. 110-42-9, log P=4.41), 2-undecanone (CAS No. 112-12-9, log P=4.21), hexane (CAS No. 110-54-3, log P=3.9), dichloromethane (CAS No. 75-09-2, Log P=1.25), 2-decanol (CAS No. 1120-06-5, log P=3.71), 4-decanol (CAS No. 2051-31-2, log P=3.71), 3-decanone (CAS No. 928-80-3, log P=3.2), 4-decanone (CAS No. 624-16-8, log P=3.2), 1-nonanol (CAS No. 143-08-8, log P=3.3), 2-nonanol (CAS No. 628-99-9, log P=3.22), 2-heptanol (CAS No. 543-49-7, log P=2.24) and mixtures thereof. All solvents of the invention are available commercially from, for example, Aldrich (Milwaukee, Wis.).

In one embodiment, an enzyme source having PDC1 activity is used with methyl decanoate, toluene, dichloromethane, 4-decanol, or mixtures thereof. In another embodiment, an enzyme source having PDC2 activity is used with toluene, methyl decanoate, 2-decanol, 4-decanone, 2-nonanol, dichloromethane or mixtures thereof.

Method for Producing pHS and Derivatives Thereof

The pHCA substrate, obtained as described above, is added to a suitable buffer solution, which serves as the aqueous phase of the biphasic reaction medium. The buffer used may be any buffer known in the art that maintains the activity of the PDC enzyme and provides buffering capacity at the desired pH, typically pH 3.5 to 8 (Cavin et al., *Appl. Environ. Microbiol.* 64:1466-1471 (1998)). In one embodiment, 0.2 M phosphate buffer, pH 6.0, containing bovine serum albumin (BSA) is used. In another embodiment involving large-scale production of pHS, a low concentration buffer or an aqueous solution without a buffer is used as the aqueous phase. In this case, the desired pH is maintained by the addition of acid or base during the course of the reaction. In the case of bioproduced pHCA, the aqueous phase may be the fermentation medium containing the PHCA, which may be used directly in the biocatalytic reaction. It may be necessary to adjust the pH and buffering capacity of the fermentation medium by addition of buffer. Alternatively, the desired pH may be maintained by the addition of acid or base during the reaction, as described above. In one embodiment, the cells and any solids present due to insoluble materials are removed from the fermentation medium to give a fermentation supernatant, which is used as the aqueous phase in the biocatalytic reaction. The cells and insoluble materials may be removed by any method known in the art, including but not limited to centrifugation or filtration. Typically, the pHCA is present in the aqueous phase at a concentration from about 30 to about 200 mM.

The enzyme source having PDC activity, as described above, is typically added from an aqueous buffer solution. The enzyme source is typically used at a concentration from about 0.01 to about 100 Units of PDC activity per milliliter of aqueous phase in the biphasic reaction medium. The amount of PDC activity is expressed in terms of a Unit, wherein one Unit will release 1 µmol of pHS per min per mL of solution using pHCA as the substrate in 25 mM phosphate buffer, pH 6.0, at 30° C.

The extractant, as described above, is added to the aqueous buffer to give a biphasic reaction medium containing from about 5% to about 70%, in addition from about 20% to about 50%, of the extractant by volume. The extractant may be added to the aqueous phase prior to, simultaneously with, or subsequent to the addition of the enzyme source. If the extractant is added subsequent to the addition of the enzyme source, it should be added as soon as possible so that the concentration of the product does not reach inhibitory levels.

The biocatalytic reaction is carried out at a temperature ranging from about 4° C. to about 60° C., in addition ranging from about 30° C. to about 45° C., in any suitable reactor. Suitable reactors for biocatalytic reactions are well known in the art (see for example Pitcher, *Immobilized Enzymes for Industrial Reactors*, Ralph A. Messing, ed., Academic Press, New York, 1975, Chapter 9, pp. 151-156; Cheetham, *Handbook of Enzyme Biotechnology*, second edition, Alan Wiseman, ed., John Wiley and Sons, New York. 1985, Part A, Chapter 3, pp. 107-116; Kent et al., *Topics in Enzyme and Fermentation Biotechnology*, Vol. 2, Alan Wiseman, ed., John Wiley and Sons, New York, 1978, Chapter 2, pp. 63-70; and references therein). Examples include stirred tank reactors, packed bed reactors, fluidized bed reactors, tubular reactors, hollow fiber reactors and biofilm reactors. In one embodiment, a stirred tank reactor is used. The reactor may be operated in batch or continuous mode. In the batch mode, the composition of the reaction medium is set at the beginning of the run and is not altered during the process. In the continuous mode, substrate and extractant are added to the reactor during the run and the biphasic reaction medium is removed. The progress of the reaction may be followed by measuring the concentration of pHS as a function of time, using thin layer chromatography (TLC), spectrophotometry, high performance liquid chromatography (HPLC) or other methods known in the art.

After completion of the reaction using the batch mode, the two phases are separated by means known in the art, including but not limited to gravity settling or centrifugation. In some cases an emulsion may form. The emulsion may be broken using methods known in the art, such as filtration or centrifugation. The enzyme source may be recovered from the aqueous phase using methods known in the art including, but not limited to ultrafiltration, nanofiltration, and the like, and then reused in a subsequent reaction. When an immobilized enzyme source is used or when the enzyme source is intact cells, the recovery of the biocatalyst is simplified. In this case the immobilized enzyme source may be recovered from the aqueous phase using filtration, centrifugation, or other methods known in the art. The product pHS may be recovered from the extractant using methods well known in the art, including, but not limited to evaporation, distillation, or adsorption by resins or molecular sieves.

In the continuous mode, biphasic reaction medium is removed continuously or periodically from the reactor. The two phases are separated by means known in the art including, but not limited to a gravity settler, a centrifuge or a hydrocyclone. An example of a gravity separator is described by Kollerup et al. in U.S. Pat. No. 4,865,973, incorporated herein by reference. The use of centrifuges and hydrocyclones is well known in the art of industrial processing (See for example, *Ullmann's Encyclopedia of Industrial Chemistry*, Fifth Edition, Elvers et al. Eds., VCH Publishers, New York, Vol. B2, Chapter 11, 1988). After separation, the aqueous phase containing the enzyme source may be recycled to the reactor. Alternatively, fresh enzyme source may be added to the reactor. If an immobilized enzyme source is used, the enzyme source in the reactor need not be replenished. The extractant is treated to recover the product by means described above. The extractant may then be recycled back into the reactor for the further extraction of the product. Alternatively, fresh extractant may be continuously added to the reactor to replace the removed extractant.

In another embodiment of the continuous mode, the aqueous phase comprising the pHCA substrate and the enzyme source is contained in a reactor and the aqueous phase is continually removed and contacted with the extractant, i.e., the organic solvent, in an external extraction column. Any of the reactors given above may be used. In this mode, the biphasic reaction medium is formed in the external column. The use of an external extraction column in fermentations and biocatalytic reactions is well known in the art (e.g., Eiteman et al. *Appl. Microbiol. Biotechnol.* 30:614-618 (1989)). The aqueous phase and the extractant are separated from the biphasic reaction medium using any of the methods given above and the aqueous phase is returned to the reactor. Alternatively, fresh aqueous phase may be added to the reactor. The extractant is treated to recover the product by means described above. The extractant may be recycled or fresh extractant may be continually added to the extraction column. Conditions must be adjusted so that the concentration of the product pHS does not reach inhibitory levels in the reactor.

In one embodiment, the pHS is chemically derivatized in the extractant before it is recovered. Any suitable chemical derivatization method known in the art may be used. Suitable derivatives of pHS include, but are not limited to, various ethers and esters. Examples of ethers and esters derived from pHS include, but are not limited to, compounds having the general formula given by:

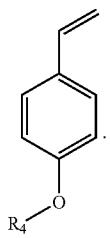

wherein $R_4$ is methyl (Hattori et al., *J. Amer. Chem. Soc.* 81:4424-4425 (1959)), t-butyl (Gable et al., *J. Amer. Chem. Soc.* 124:3970-3979 (2002)), alkyl (Hassanein et al., *J. Org. Chem.* 54:3106-3113 (1989)), silyl ethers (Nakahama et al., *Prog. Polym. Sci.* 15:299-335 (1990)), allyl (Woods et al., U.S. Pat. No. 5,633,411), t-butoxy carbonyl (Nader et al., U.S. Pat. No. 5,082,965), hydroxyethoxy (Inokuma et al., *Heterocycles* 40:401-411 (1995)), acetoxy (Sounik et al., U.S. Pat. No. 5,463,108), formate (Tessier et al., *Materials for Microlithography: Radiation-Sensitive Polymers*, ACS Symposium Series 266, American Chemical Society, Washington, D.C., 1984), glycidyl (Ericsson et al., U.S. Pat. No. 6,255,385), benzoate (Hattori et al., *J. Amer. Chem. Soc.* 81:4424-4425 (1959)), phenylcarbonate (Whitcombe et al., *J. Amer. Chem. Soc.* 117:7105-7111)), tetrahydropyran (Menzier et al., *Bioorg. Med. Chem. Lett.* 10:345-348 (2000)), benzyl (Kotecha et al., *Synlett.* 1992:395), or poly (ethylene oxide) (Inokuma et al., *Heterocycles* 54:123-130 (2001)). The references cited in parentheses, all of which are incorporated herein by reference, describe methods that may be used to synthesize the cited derivative. In another embodiment, the pHS is polymerized to poly(para-hydroxystyrene) and other copolymers using the methods described by Kaneko et al. in U.S. Pat. Nos. 5,959,051 and 6,258,901, both of which are incorporated herein by reference. In another embodiment, the pHS derivative is para-acetoxystyrene, which may be prepared using the method described by Sounik et al. in U.S. Pat. No. 5,463,108. Following derivatization, the derivatized product is recovered from the extractant using the methods described supra.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "rpm" means revolutions per minute, "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmol" means micromole(s), "g" means gram(s), "µg" means microgram(s), "mg" means milligram(s), "bp" means base pairs, "kbp" means kilobase pairs, "kPa" means kilopascals, "OD" means optical density, "$OD_{600}$" means the optical density at a wavelength of 600 nm, "$OD_{550}$" means the optical density measured at a wavelength of 550 nm, "TLC" means thin layer chromatography, "$R_f$" means retardation factor, i.e., the ratio of distance traveled by the center of a zone to the distance simultaneously traveled by the mobile phase in TLC, "HPLC" means high performance liquid chromatography, "UV/VIS" means spectrophotometry in the ultraviolet and visible wavelength range, "NMR" means nuclear magnetic resonance, "MHz" means megahertz, "$A_{315}$" means the absorbance measured at a wavelength of 315 nm, "$\Delta A_{315}$" means the change in absorbance measured at 315 nm, "IPTG" means isopropyl β-D-thiogalactopyranoside, "X-gal" means 5-bromo-4-chloro-3-indolyl-beta-D-galactopyranoside, "psi" means pounds per square inch, "g" is the gravitation constant, "kV" means kilovolt(s), "µF" means microfarad(s), "w/v" means weight of solute per volume of solution, and "w/w" means weight of solute per weight of solution.

General Methods:

Materials and methods suitable for the maintenance and growth of bacterial cultures are well known in the art. Techniques suitable for use in the following Examples may be found as set out in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C. (1994) or by Thomas D. Brock in *Biotechnology: A Textbook of Industrial Microbiology*, Second Edition, SinauerAssociates, Inc., Sunderland, Mass. (1989). All reagents and materials used for the growth and maintenance of bacterial cells were obtained from Aldrich Chemicals (Milwaukee, Wis.), BD Diagnostics Systems (Sparks, Md., formerly DIFCO Laboratories), Invitrogen Life Technologies (Carlsbad, Calif., formerly GIBCO/BRL), or Sigma Chemical Company (St. Louis, Mo.) unless otherwise specified.

All chemicals were reagent-grade and used as received from the manufacturer or distributor. Unless otherwise noted, the biochemicals were obtained from Sigma Chemical Company and dehydrated media were obtained from BD Diagnostics Systems. All solvents were obtained from Aldrich Chemicals. The water was bottled, spectroscopic grade water from either EM Science (Gibbstown, N.J.) or Aldrich Chemicals. We used the supplies from various manufacturers interchangeably. All of the chromatography resins were prepared and maintained according to the instructions provided by the manufacturer.

The LB culture medium used in the Examples contains the following per liter of medium: Bacto-tryptone (10 g), Bacto-yeast extract (5 g), and NaCl (10 g).

The non-recombinant organisms used in the present invention were obtained from the American Type Culture Collection (ATCC, Manassas, Va.). These cultures were transformed from a lyophilized state to a suspension culture in appropriate medium and maintained in 15% glycerol for long-term storage at −80° C.

All operations that involved the growing of organisms were performed at 37° C. in a New Brunswick incubator shaker Model G25 3 (New Brunswick Scientific Co., Edison, N.J.), unless otherwise noted. Cell-free extracts were prepared by resuspending the cells to an optical density of 35 or 70 optical density ($OD_{600}$) units per mL in 25 mM sodium phosphate, pH 6.0 buffer and lysing the cells by passage through a French pressure press.

Analysis of PHCA and pHS:

The analysis of mixtures of pHCA and pHS was performed using one or more of the following techniques, TLC, UV/VIS spectrophotometry, and HPLC. TLC was done using Silica gel $60F_{254}$ (Merck, Darmstadt, Germany) as the solid support and 100% ethyl acetate as the mobile phase. HPLC was performed with a photodiode array detector and a Zorbax 300 Stable Bond Analytical SB-C18 column (4.6× 150 mm, Agilent Technologies, Wilmington, Del.). The HPLC separation was achieved using a gradient combining two solvents: Solvent A, 0.1% trifluoroacetic acid in HPLC grade water and Solvent B, 0.1% trifluoroacetic acid in acetonitrile. The mobile phase flow rate was 1.0 mL/min. The solvent gradient used is given in Table 1.

TABLE 1

Solvent Gradient Used for HPLC

| Time (min) | Solvent A | Solvent B |
|---|---|---|
| 0 | 95% | 5% |
| 8 | 20% | 80% |
| 10 | 20% | 80% |
| 15 | 95% | 5% |

Isolated pHS was analyzed by $^1$H NMR spectroscopy at 500 MHz.

Determination of PHCA Decarboxylase Activity:

Decarboxylase activity was measured using an assay whose principles were described previously by Cavin et al. in *FEMS Microbiol. Lett.* 147:291-295 (1997). The conversion of pHCA was followed by recording absorbance changes at 315 nm ($A_{315}$) against a reference beam of air. The assay buffer consisted of 0.2 mM pHCA in 25 mM sodium phosphate, pH 6.0 buffer in a 1.0 cm semi-microcuvette thermostated at 30° C. The enzyme extract was added to initiate the decarboxylation reaction. The initial rate was recorded as the change in $A_{315}$ ($\Delta A_{315}$) and the enzyme activity in Units/mL (where one Unit will release 1 µmol of product per min per mL of solution) were calculated by the following conversion formula:

$$Units/mL = \frac{(\text{Dilution factor}) \times (\Delta A_{315})}{10 \times \text{extract volume} \times 1\text{cm}}$$

The molar absorptivity coefficient for pHCA was empirically determined at 315 nm to be 10 $cm^{-1}$ $mM^{-1}$.

Protein concentrations were determined using a BioRad kit (BioRad Laboratories, Hercules, Calif.) for protein determination. A protein standard curve was generated using five protein standards ranging from 100 to 800 µg/mL bovine serum albumin (BSA) solutions. The microtiter plate assay format was used which required the addition of 10 µL of sample to 160 µL of the BioRad reagent.

Example 1

Production of Cell-Free Extracts of PDC1 and PDC2 Enzymes from *E. coli* Overexpressing Strains The purpose of this Example was to produce cell-free extracts of the para-hydroxycinnamic acid decarboxylase enzymes PDC1 (*Lactobacillus plantarum*) and PDC2 (*Bacillus subtilis*) from *E. coli* overexpressing strains. Two plasmids, pET17.pdc1 and pET17.pdc2, were constructed that overexpress the PDC1 and PDC2 enzymes, respectively. These plasmids were used to transform *E. coli* strain BL21 to produce the two overexpressing strains that had high percentages of decarboxylase protein and activity. The cell-free extracts were obtained by lysing the cells using a French press.

Construction of PDC1 and PDC2 *E. coli* Overexpressing Strains:

The pdc genes, pdc1 (SEQ ID NO:1) and pdc2 (SEQ ID NO:3), were amplified by PCR using genomic DNA from *L. plantarum* and *B. subtilis*, respectively, as templates. The genomic DNA was isolated from *L. plantarum* grown on MRS medium and *B. subtilis* grown on LB medium using a DNeasy® Kit (Qiagen, Valencia, Calif.). The oligonucleotide primers used for the pdc1 gene, para-coumaric acid decarboxylase (GenBank Accession no. U63827), from *L. plantarum*, were 5'-GGTMTT<u>CATATG</u>ACAAA-3' given as SEQ ID NO:5 and 5'-TCACGTGAAACATTACTTATT-3' given as SEQ ID NO:6, which included a NdeI site (underlined nucleotides). The oligonucleotide primers used for the *B. subtilis* pdc2, phenolic acid decarboxylase (GenBank Accession no. AF-17117), were 5'-GTGTGT<u>CATATG</u>GAAAACT-3' given as SEQ ID NO:7 and 5'-TCGCGGGAATTGTGATGGT-3' given as SEQ ID NO:8, which also included a NdeI site (underlined nucleotides). The expected 550-bp DNA fragments for both pdc1 and pdc2 genes were purified using a Qiagen PCR Clean Up Kit and were ligated into the pCRII-TOPO cloning vector using the TA Cloning® Kit from Invitrogen. The transformations were done using One Shot® Chemically Competent *E. coli* (Invitrogen) according to the manufacturer's directions, except that 2xYT medium (Invitrogen) was used instead of SOC. The transformed cells were spread onto 50 µg/mL ampicillin plates containing X-gal and IPTG. From each of these plates, 10 white colonies were selected and restreaked onto ampicillin plates. The following procedures were done using cells transformed with pdc1 and cells transformed with pdc2 genes.

Each of the colonies was grown overnight on LB medium containing 50 μg/mL ampicillin. The plasmid was purified from the cells using the Qiagen Miniprep Kit. The plasmid was digested for 1 h at 37° C. with EcoRI to test for the presence of the insert. The digests were loaded on 1% agarose gels, along with kilobase markers, and electrophoresis was performed. Two bands were observed on the resulting gels, one at approximately 550 bp, corresponding to the insert, and one at 3.9 kbp, corresponding to the vector.

The cells containing the vector from one of the minipreps was grown overnight in a 50 mL culture containing 50 μg/mL ampicillin. The vector was purified from these cells using the Qiagen Midiprep QIAfilter according to the manufacturer's directions. The plasmid resulting from the *Lactobacillus plantarum* pdc gene was designated PDC1, while the plasmid resulting from the *Bacillus subtilis* pdc gene was designated pDC2. The inserts were sequenced at the DuPont Sequencing Facility using M13 forward and reverse primers in the vector to confirm the sequences. Computer analyses of the sequences were carried out by using Vector NTI (InforMax, Inc., Frederick, Md.) software.

The plasmid pDC1 was digested for 4 h at 37° C. using NdeI and EcoRI. The plasmid pDC2 was digested for 4 h at 37° C. using NdeI and NotI. The digests were loaded onto 1% agarose gels, along with kilobase markers, and electrophoresis was performed. A 555 bp band, corresponding to the insert, and a 3.9 kbp band, corresponding to the vector, were observed for the digest of pDC1. A 583 bp band, corresponding to the insert and a 3.9 kbp band, corresponding to the vector, were observed for the digest of pDC2. The insert bands were cut from the gel and purified using the Qiagen Gel Extraction Kit according to the manufacturer's protocol. The pET-17b vector, obtained from Novagen, Inc. (Madison, Wis.) was digested as described above and run on a 1% agarose gel. The vector band at 3.3 kbp, corresponding to the cut vector, was cut from the gel and purified using the Qiagen Gel Extraction Kit according to the manufacturer's protocol.

The pDC1 insert and the cut vector were ligated using T4 DNA ligase. Similarly, the pDC2 and the cut vector were ligated. The reactions were incubated for 1 h at room temperature. The resulting plasmids are herein referred to as pET17.pdc1 and pET17.pdc2. The plasmids pET17.pdc1 and pET17.pdc2 overexpress the PDC1 and PDC2 enzymes, respectively, under the control of a strong T7 promoter. *E. coli* strain BL21(DE3) [genotype: recA1 endA1 hsdR17 supE44 thi-1 gyrA96 relA1 f80IacZ dM15 d(lacZYA-argF) U169 (DE3)], obtained from Stratagene (La Jolla, Calif.) was used as the host strain for the high-level protein expression using T7 RNA polymerase-based expression systems. The strain designated as DPD5004 was constructed by transforming plasmid pET17.pdc1 into BL21 (DE3); the strain designated as DPD5005 was constructed by transforming plasmid pET17.pdc2 into BL21 (DE3). To construct strain DPD5004, plasmid pET17b.pdc1 (0.1 μg) was added into 50 μL of BL21(DE3) chemical competent cells (Stratagene). This mixture was incubated on ice for 30 min, treated by heat shock at 42° C. for 45 s, put back on ice for 2 min, and then resuspended in SOC medium (Invitrogen, Carslbad, Calif.). The cells were incubated at 37° C. for 1 h before plating onto an LB plate containing 100 μg/mL ampicillin. Similarly, strain DPD5005 was constructed by transforming pETb.pdc2 into BL21(DE3). The expression of PDC enzymes was induced by IPTG, which initiates expression of the enzyme T7 RNA polymerase, which in turn activates the gene transcription of the T7 promoter-controlled pdc1 and pdc2 genes.

Growth of *E. coli* Overexpressing Strains and Preparation of Cell-Free Extracts of PDC1 and PDC2:

Overnight cultures of *E. coli* strains DPD5004 and DPD5005 were grown from −80° C. glycerol stocks in LB broth containing 150 μg/mL ampicillin (LB-amp). In a typical experiment, a 2 mL overnight culture was used to inoculate each of four, 0.5 L flasks containing 100 mL of LB-amp. The cultures were grown to an $OD_{600}$ of 0.5 and were induced by addition of IPTG to a final concentration of 0.5 mM. The cultures were grown for 60 min before the cells were harvested by centrifugation (20 min, 10,000×g at 4° C.) affording a cell paste of 1.1 g. The cell pastes were stored at 4° C. until further use.

To prepare cell-free extract, a thawed cell paste was resuspended in standard working buffer (25 mM sodium phosphate, pH 6.0 buffer) to a density of $700D_{600}/mL$ and was lysed by passing the suspension through a French pressure cell (1200 psi). The lysate was centrifuged and the supernatant was retained. The resulting percentages of the enzyme in the total protein were determined by measuring the density of protein bands on a 10-20% SDS-PAGE gel stained with Coomassie Blue. The decarboxylase activity was measured as described in the General Methods section, supra. These results are summarized in Table 2.

TABLE 2

Amount and Activity of the Decarboxylase Protein Expressed in the *E. coil* Overexpressing Strains

| Gene | Strain | Plasmid | Decarboxylase protein expressed (% of total protein) | Activity (U/mL) | Specific Activity (U/mg) |
|---|---|---|---|---|---|
| pdc1 | E. coli 5004 | pET17b.pdc1 | 12.9 | 15.3 ± 8.7* | 3.5 ± 1.9* |
| pdc2 | E. coli 5005 | pET17b.pdc2 | 31.3 | 133 ± 71** | 19 ± 6** |

*Mean and standard deviation of 4 cell-free extract preparations
**Mean and standard deviation of 3 cell-free extract preparations Example 2

Decarboxylase Activity of PDC2 Cell-Free Extract in a Biphasic Reaction Medium

The purpose of this Example was to demonstrate the advantage of using the PDC2 cell-free extract to produce pHS in a biphasic reaction medium. The retention of PDC2 enzymatic activity was measured in aqueous/toluene, aqueous/dichloromethane, and aqueous/methyl decanoate biphasic reaction media.

A glass scintillation vial containing a small stir bar was charged with 5 mL of one of the following water-immiscible organic solvents, spectral grades of toluene, dichloromethane, or methyl decanoate. Then, 10 mL of a PHCA substrate solution (30 to 120 mM PHCA solution in 0.2 M sodium phosphate, pH 6.0 with 1.2 mg/mL BSA) and 15 μL of PDC2 cell-free extract (150 μg protein; 15 Units), prepared as described in Example 1, were added. The vial was capped, placed on a magnetic stir plate and vigorously stirred. The reaction was allowed to proceed for a time period sufficient for conversion of the pHCA to pHS. During the course of the reaction, the reaction progress was monitored by TLC, UV/VIS, and HPLC, as described in the General Methods section, supra. The pHCA and pHS migrated with $R_f$ values of 0.4 and 0.7, respectively on the TLC plates. When the reaction was completed, the contents were transferred to a 60 mL separatory funnel and the layers were allowed to separate. The aqueous layer was recovered and immediately filtered by ultrafiltration using a YM-10 membrane (Millipore Corp., Billerica, Mass.) to separate and recover the enzyme. This first aqueous filtrate was retained and analyzed by HPLC to verify depletion of the PHCA substrate. The protein and decarboxylase-containing retentate was washed twice with 0.2 M sodium phosphate, pH 6.0 buffer using the ultrafiltration membrane and the retentate from the second wash was resuspended to the original reaction volume. The residual enzyme activity was determined using the pHCA decarboxylase assay described in the General Methods section, supra, using a 50 µL volume of the suspension.

After the enzyme assay, the sample was treated by ultrafiltration and the PDC2 enzyme was resuspended in a volume of pHCA-containing buffer solution equivalent to the aqueous layer volume at the end of the previous reaction. The restored enzyme solution was immediately added to a volume of unspent organic solvent and the suspension was stirred. The above steps were repeated until the reaction time for complete conversion of PHCA to pHS had doubled relative to the initial reaction time. The results of the enzyme assays performed after each cycle are shown in Table 3. As can be seen from the data in the Table, the retention of enzymatic activity was highest in the aqueous/toluene system. Moreover, the retention of enzymatic activity was much higher than that obtained in a single-phase aqueous system, as shown in comparative Example 3.

TABLE 3

Residual Decarboxylase Activity in Successive Recycles of PDC2 Cell-Free Extracts in Different Biphasic Reaction Media

| Cycle No. | Residual decarboxylase activity in aqueous/toluene (%) | Residual decarboxylase activity in aqueous/dichloromethane (%) | Residual decarboxylase activity in aqueous/methyl-decanoate (%) |
|---|---|---|---|
| 0 | 100 | 100 | 100 |
| 1 | 90 | 83.5 | 73.9 |
| 2 | 86 | 76.5 | 24.2 |
| 3 | 73 | 72.4 | 1.8 |
| 4 | 76 | 47.5 | 2.3 |
| 5 | 56 | — | — |
| 6 | 47 | — | — |
| 7 | 41 | — | — |
| 8 | 36 | — | — |
| 9 | 34 | — | — |

The organic layers from two toluene reactions were analyzed by TLC and HPLC. Then, the two organic layers were pooled and transferred to a 25 mL pear-shaped round-bottomed flask. A minute quantity of polymerization inhibitor, 2,6-di-t-butyl-4-methyl-phenol (CAS 98-29-3; Aldrich 12,424-9) was added to the clear, colorless toluene solution. An ivory-white crystalline solid (44 mg) was recovered by rotary evaporation under vacuum (200 mm Hg) with mild heating (45° C.). The isolated solid was characterized by proton NMR (4 mg dissolved in 0.8 mL of perdeuterated methanol). The purity of the pHS produced was determined to be greater than 98 percent. Further purification of the product was achieved by recrystallization from hexane to recover a white crystalline solid. This result demonstrates the ease of isolation of the pHS produced from the organic layer.

$^1$H-NMR (d4-MeOH): 7.3 ppm, doublet, 2H, (5,6-protons of Aromatic ring); 6.78 ppm, doublet, 2H, (2,3-protons of aromatic ring); 6.65 ppm, multiplet, 1H (Ar—HC=CH2); 5.6 ppm, doublet, 1H, (Ar—C=CH, cis); 5.05 ppm, doublet, 1H (Ar—C=CH, trans).

Example 3

Comparative Example of the Decarboxylase Activity of PDC2 Cell-Free Extract in a Single-Phase Aqueous Reaction Medium The purpose of this Example was to measure the retention of enzymatic activity of PDC2 cell-free extract in a single-phase aqueous reaction medium to serve as a comparison for the biphasic reaction medium described in Example 2.

A glass scintillation vial containing a small stir bar was charged with 10 mL of pHCA solution (30 mM pHCA solution in 0.2 M sodium phosphate, pH 6.0 with 1.2 mg/mL BSA). Then, 15 µL of PDC2 cell-free extract (150 µg protein, 15 Units), prepared as described in Example 1, was added to initiate the reaction. The vial was capped, placed on a magnetic stir plate and was vigorously stirred. The reaction was allowed to proceed for a time period sufficient for the complete conversion of the pHCA to pHS. During the course of the reaction, the reaction progress was monitored by TLC, UV/VIS and HPLC, as described in the General Methods section, supra. Under these conditions, the $R_f$ values for pHCA and pHS were 0.4 and 0.7, respectively. When the reaction was completed or did not proceed further, the enzyme was recovered by ultrafiltration using a YM10 membrane, as described in Example 2. The filtrate was washed several times to remove any residual pHCA or pHS. After the washes, the filtrate was restored to its final reaction volume, the residual activity was determined as described in Example 2, and then the steps outlined above were repeated until there was no detectable decarboxylase activity. The results of the enzyme assays performed after each cycle are shown in Table 4. As can be seen from the data in the Table, the retention of enzymatic activity was much lower than that obtained in Example 2 where a biphasic reaction medium was used. This Example demonstrates the advantage of using the PDC2 enzyme to produce pHS in a biphasic reaction medium.

TABLE 4

Residual Decarboxylase Activity in Successive Recycles of PDC2 Cell-Free Extract in a Single-Phase Aqueous System

| Cycle No. | Residual Enzyme activity (%) | Units in reaction |
|---|---|---|
| 0 | 100 | 14.1 |
| 1 | 22 | 3.05 |
| 2 | 20 | 2.85 |
| 3 | 9.5 | 1.34 |
| 4 | 5.2 | 0.74 |

Example 4

Production of pHS using PDC1 Cell-Free Extract in a Biphasic Reaction Medium

The purpose of this Example was to demonstrate the production of pHS using PDC1 cell-free extract in a biphasic reaction medium. The retention of PDC1 enzymatic activity was measured in aqueous/toluene, aqueous/dichloromethane, aqueous/methyl decanoate, and aqueous/2-undecanone biphasic reaction media.

A glass scintillation vial containing a small stir bar was charged with 5 mL of one of the following water-immiscible organic solvents, spectral grades of toluene, dichloromethane, methyl decanoate, or 2-undecanone. Then, 10 mL of a PHCA substrate solution (30 to 120 mM pHCA solution in 0.2 M sodium phosphate, pH 6.0, containing 1 mg/mL BSA) and 500 µL of PDC1 cell-free extract (2.15 mg protein; 15 Units), prepared as described in Example 1, were added. The vial was capped, placed on a magnetic stir plate and vigorously stirred. During the course of the reaction, the reaction progress was monitored by TLC, UV/VIS and HPLC, as described in the General Methods section, supra. When pHCA was depleted or the reaction ceased, the contents were transferred to a 60 mL separatory funnel and the layers were allowed to separate. The aqueous layer was immediately filtered by ultrafiltration to separate and recover the enzyme from the product and reactants. The biocatalysis reaction was repeated in cycles in a manner identical to that described in Example 2. The results of the enzyme assays performed after each cycle are shown in Table 5. As can be seen from the data in the Table, the retention of enzymatic activity was high in both the aqueous/toluene biphasic medium and the aqueous/methyl decanoate biphasic medium.

TABLE 5

Residual Decarboxylase Activity in Successive Recycles of PDC1 Cell-Free Extracts in Different Biphasic Reaction Media

| Cycle No. | Residual Enzyme activity in aqueous/toluene (%) | Residual Enzyme activity in aqueous/methyl decanoate (%) | Residual Enzyme activity in aqueous/dichloromethane (%) | Residual Enzyme activity in aqueous/2-undecanone |
|---|---|---|---|---|
| 0 | 100 | 100 | 100 | 100 |
| 1 | 101 | 95 | 43[a] | 61[a] |
| 2 | 117 | 72 | — | — |
| 3 | 86 | 72 | — | — |
| 4 | 63 | 63 | — | — |
| 5 | 55 | 61 | — | — |
| 6 | 60 | 27 | — | — |
| 7 | 35 | 39 | — | — |
| 8 | 30 | 16 | — | — |
| 9 | 15 | 3 | — | — |

[a]Values were averages of two independent experiments.

Example 5

Production of pHS using PDC1 Cell-Free Extract in a Biphasic Reaction Medium

The purpose of this Example was to demonstrate the production of pHS from pHCA using PDC1 cell-free extract in a biphasic reaction medium and to demonstrate the convenient recovery of the pHS from the organic layer.

A 0.5 L jacketed Wheaton CelStir® reactor (Wheaton Science Products, Millville, N.J.) was charged with 0.280 L of pHCA (5 g/L) in 0.2 M sodium phosphate, pH 6.0 buffer and 15 mL of bovine serum albumin (20 mg/mL). Cell-free extract containing PDC1 (2.5 mL, 13 mg protein, 69.5 Units), prepared as described in Example 1, was added along with 0.15 L of toluene. The reactor was capped, placed on a magnetic stir plate and stirred at moderate speeds. The reaction temperature was set at 33° C. The reaction was allowed to proceed for 30 min, after which the reaction was terminated because it appeared to be completed by TLC. The pHS produced was isolated as described in Example 4. The ivory-colored residue (1.1 g) was recrystallized, collected into a vial and dried under high vacuum (60 mm Hg) to constant dryness and characterized by $^1$H-NMR analyses in perdeuterated methanol. The proton NMR results showed chemical shift values consistent with pHS and the purity was assessed at 98%. This Example demonstrates the convenient recovery of pHS from the organic layer of the PDC1-catalyzed reaction in a biphasic reaction medium.

Example 6

Production of PHS using PDC1 Cell-Free Extract and Bioproduced pHCA-Containing Fermentation Medium in a Biphasic Reaction Medium The purpose of this Example was to demonstrate the production of pHS using PDC1 cell-free extract and pHCA, contained in a fermentation medium, using a biphasic reaction medium. The pHCA was first produced by fermentation using a recombinant strain of *E. coli* (DPD4009). The pHCA was then converted to pHS in a biphasic reaction medium, consisting of fermentation supernatant and toluene, using PDC1 cell-free extract.

Construction of *E. coli* Strain DPD4009

*E. coli* strain DPD4009 is a tyrosine-overproducing, plasmid-less, phenylalanine auxotroph, which was derived in several steps from *E. coli* TY1 (DGL430), a tyrosine overproducing strain obtained from OmniGene Bioproducts, Inc. (Cambridge, Mass.). First, TY1 was cured of the plasmid it was carrying to yield a tetracycline-sensitive strain called TS5. Subsequently, TS5 was the recipient in a P1-mediated transduction using *E. coli* strain CAG12158, which carries pheA18::Tn10 (Coli Genetics Stock Center, Yale University, #7421), as the donor. One tetracycline-resistant transductant was called BNT565.2.

*E. coli* strain WS158 was constructed using the two PCR fragments integration method described by Suh in U.S. Patent Application No. 60/434,602, incorporated herein by reference, via λ-Red recombinase system. A first linear DNA fragment (1581 bp) containing a kanamycin selectable marker flanked by site-specific recombinase target sequences (FRT) was synthesized by PCR from plasmid pKD4 (Datsenko and Wanner, *Proc. Natl. Acad. Sci.* 97:6640-6645 (2000)) with primer pairs, T-kan(tyrA) (5'-AATTCATCAGGATCTGAACGGGCAGCTGACGGCTC GCGTGGCTTAAC GTCTTGAGCGATTGTGTAG-3') (SEQ ID NO:9) which contains a homology arm (underlined, 46 bp) chosen to match sequences in the upstream region of the aroF stop codon and a priming sequence (20 bp), and B-kan(trc) (5'-AAAACATT ATCCAGAACGGGAGTGCGCCTTGAGCGACACGAA TATGA ATATCCTCCTTAGTTCC-3') (SEQ ID NO:10) that contains a homology arm (underlined, 42 bp) chosen to match sequences in the 5'-end region of the Ptrc promoter DNA fragment and a priming sequence (22 bp). A second linear DNA fragment (163 bp) containing a Ptrc promoter comprised of the −10 and −35 consensus sequences, lac operator (lacO), and ribosomal binding site (rbs) was synthesized by PCR from plasmid pTrc99A (Invitrogen, Carlsbad, Calif.) with primer pairs, T-trc(kan) (5'-CTAAGGAGGATATTCATATTCGTGTCGCTCAAGGC GCACT-3') (SEQ ID NO:11) that contains a homology arm (underlined, 18 bp) chosen to match sequences in the downstream region of the kan open reading frame and a priming sequence (22 bp), and B-trc(tyrA) (5'-CGACTTCATCAATTTGATCGCGTAATGCGGTCAATT CAGCAACCATG GTCTGTTTCCTGTGTGAAA-3') (SEQ ID NO:12) that contains a homology arm (underlined, 46 bp) chosen to match sequences in the downstream region of the tyrA start codon and a priming sequence (20 bp). The underlined sequences illustrate each respective homology arm, while the remainder is the priming sequences for hybridization to complementary nucleotide sequences on the template DNA for the PCR reaction. Standard PCR conditions were used to amplify the linear DNA fragments using the MasterAmp™ Extra-Long PCR kit (Epicentre, Madison, Wis.) as follows. The PCR reaction mixture contained 1 μL of plasmid DNA, 25 μL of 2×PCR buffer #1, 1 μL of the 5'-primer (20 μM), 1 μL of the 3'-primer (20 μM), 0.5 μL of MasterAmp™. Extra-Long DNA polymerase, and 21.5 μL of sterilized, deionized H$_2$O. The PCR reaction conditions were: 94° C. for 3 min; 25 cycles of 93° C. for 30 sec, 55° C. for 1 min, and 72° C. for 3 min; followed by 72° C. for 5 min. After completing the PCR reactions, the PCR products were purified using the Mini-elute QIAquick Gel Extraction Kit™ (QIAGEN Inc. Valencia, Calif.). The DNA was eluted with 10 μL of distilled water by centrifuging twice at high speed. The concentration of the isolated PCR product was about 0.5-1.0 μg/μL.

E. coli MC1061 strain carrying a λ-Red recombinase expression plasmid was used as a host strain for the recombination of PCR fragments. This strain was constructed by transformation with a λ-Red recombinase expression plasmid, pKD46 (amp$^R$) (Datsenko and Wanner, supra) into E. coli strain MC1061 (Coli Genetics Stock Center, Yale University, #6649). The λ-Red recombinase in pKD46 is comprised of three genes exo, bet, and gam, expressed under the control of an arabinose-inducible promoter. Transformants were selected LB plates containing 100 μg/mL ampicillin at 30° C. The electro-competent cells of E. coli MC1061 strain carrying pKD46 were prepared as follows. E. coli MC1061 cells carrying pKD46 were grown in SOB medium (Hanahan, *DNA Cloning: A Practical Approach*, D. M. Glover, ed., IRL Press, Washington, D.C., 1985, pp. 109-125) with 100 μg/mL ampicillin and 1 mM L-arabinose at 30° C. to an OD$_{600}$ of 0.5, followed by chilling on ice for 20 min. Bacterial cells were centrifuged at 4,500 rpm using a Sorvall® RT7 PLUS (Kendro Laboratory Products, Newton, Conn.) for 10 min at 4° C. After decanting the supernatant, the pellet was resuspended in ice-cold water and centrifuged again. This process was repeated twice and the cell pellet was resuspended in 1/100 volume of ice-cold 10% glycerol.

Both the kanamycin marker PCR products (~1 μg) and Ptrc promoter PCR products (~1 μg) were mixed with 50 μL of the competent cells and pipetted into a pre-cooled electroporation cuvette (0.1 cm) on ice. Electroporation was performed using a Gene Pulser System (Bio-Rad Laboratories, Hercules, Calif.) set at 1.8 kV, 25 μF with the pulse controller set at 200 ohms. SOC medium (1 mL) was added after electroporation. The cells were incubated at 37° C. for 1 h. Approximately one-half of the cells were spread on LB plates containing 25 μg/mL kanamycin. After incubating the plate at 37° C. overnight, six kanamycin resistant transformants were selected.

The chromosomal integration of both the kanamycin selectable marker and the Ptrc promoter in front of the tyrA gene was confirmed by PCR analysis. A colony of transformants was resuspended in 25 μL of PCR reaction mixture containing 23 μL of SuperMix (Invitrogen), 1 μL of 5'-primer T-ty(test) (5'-CAACCGCGCAGTGAAAT-GAAATACGG-3') (SEQ ID NO:13) and 1 μL of 3'-primer B-ty(test) (5'-GCGCTCCGGAACATAAATAGGCAGTC-3') (SEQ ID NO:14). The test primers were chosen to amplify regions located in the vicinity of the integration region. PCR analysis with the T-ty(test) and B-ty(test) primer pair revealed the expected size fragment, i.e., 1,928 bp on a 1% agarose gel. The resultant recombinant is designated herein as E. coli WS158.

Strain BNT565.2, prepared as described above, was then used as the recipient in another P1-mediated transduction with phage grown on E. coli strain WS158 that carries Ptrc-tyrA [KanR], a chromosomal modification resulting in the strong trc promoter driving tyrA expression. The pheA and tyrA genes are tightly linked on the chromosome, so selection was made for rare transductants that were resistant to both tetracycline and kanamycin. One such transductant was called DPD4009, which was shown to require phenylalanine for growth and to excrete tyrosine.

Bioproduction of pHCA

The bioproduction of pHCA was done in a 14 L Braun fermentor, BioStat C. B. (Braun Biotech International, Melesungen, Germany). The fermentation run was done using E. coli strain DPD4009, constructed as described above. The fermentation medium was a defined medium containing salts, vitamins and glucose, as given in Table 6. The composition of the trace elements solution is given in Table 7. The temperature was maintained at 35° C. and dissolved oxygen was targeted at a setpoint of 25%. The pH setpoint was 6.5 and was maintained constant with the addition of 40% (w/v) ammonium hydroxide and 20% (w/v) phosphoric acid for base and acid adjustment, respectively. When the cell density reached 10 OD$_{550}$ units, IPTG was added to a final concentration of 1 mM to the medium to induce the cells to express the phenylalanine ammonia lyase (pal) gene on the plasmid, resulting in the conversion of tyrosine to pHCA. Additional glucose was added in a fed batch mode once the concentration fell below 5 g/L. The glucose solution 60% (w/w) was added at a rate of 0.45 g/min, which kept the glucose concentration below 0.5 g/L. Lower rates were used toward the end of the run once the glucose concentration rose above 0.5 g/L. The fermentation typically ended after 72 h.

The pHCA-rich supernatant for use in the biocatalytic conversion to pHS was prepared by centrifuging the fermentation medium to separate the cells and other insoluble products. The pellet was discarded and the dark brown supernatant was transferred to a fresh storage bottle, capped and stored at 4° C. until use in the PDC biocatalysis reaction.

TABLE 6

Defined Medium for pHCA Fermentations

| Component | Amount per 7.5 L H$_2$O* |
|---|---|
| (NH$_4$)$_2$SO$_4$ | 8 g |
| Na$_2$HPO$_4$ | 17 g |
| Thiamine | 8 mg |
| Mazu DF204 (BASF Corp., Mount Olive, NJ) | 8 mL |
| Phenylalanine | 320 mg |
| KH$_2$PO$_4$ | 7 g |
| MgSO$_4$·7H$_2$O | 4 g |
| Glucose 60% | 267 g |
| Ampicillin 25 mg/mL | 32 mL |
| Trace elements | 160 mL |

*At the end of the fed batch run the fermentation medium volume reached 9-10 L.

TABLE 7

Trace Elements Solution

| Chemical | Concentration (g/L) |
|---|---|
| Citric acid | 10 |
| $CaCl_2 \cdot 2H_2O$ | 1.5 |
| $FeSO_4 \cdot 7H_2O$ | 5 |
| $ZnSO_4 \cdot 7H_2O$ | 0.39 |
| $CuSO_4 \cdot 5H_2O$ | 0.38 |
| $CoCl_2 \cdot 6H_2O$ | 0.2 |
| $MnCl_2 \cdot 4H_2O$ | 0.3 |

Production of PHS using PDC1 Cell-Free Extract

A 0.5 L jacketed Wheaton CeiStir® reactor was charged with 0.1 L of the fermentation supernatant from the PHCA fermentation, described above. During storage, some insoluble by-products may settle out of the fermentation supernatant. The supernatant was decanted into a graduated cylinder, taking care not to disturb the insoluble material. The fermentation supernatant contained pHCA (3.3 g/L), cinnamic acid (CA), phenylalanine, tyrosine (all produced by the recombinant E. coli cells), and salts at pH 6.8. The buffering capacity and the PHCA concentration were increased by adding 0.2 L of 25 g/L PHCA in 0.2 M sodium phosphate, pH 6.0 buffer. The final concentration of PHCA in the aqueous phase was approximately 17.7 g/L.

Cell-free extract containing PDC1 (0.5 mL, 1.1 mg protein, 12 Units), prepared as described in Example 1, was added along with 0.15 L of toluene. The reactor was capped, placed on a magnetic stir plate and stirred at moderate speed. The reaction temperature was set at 33° C. The reaction was allowed to proceed for 15 h before terminating. The aqueous layer retained the deep dark-brown color of the original fermentation media. The remaining emulsified organic phase was a pale yellow. The emulsion was broken by filtration through a glass-fritted funnel of medium porosity and the organic and aqueous layers were again separated. The organic layer was dried over magnesium sulfate and the pHS was isolated as described in Examples 4 and 5. About 2 g of crude solid was isolated. The solid was recrystallized from hexane, filtered through a fine pore glass-fritted funnel, collected into a vial and dried under high vacuum (60 mm Hg) to constant dryness (1.102 g). The overall yield of this reaction was 1010 g pHS produced per g of cell-free extract. This Example illustrates the ability of PDC1 decarboxylase to catalyze pHS formation with high productivity in the presence of crude fermentation components and high PHCA concentration.

Example 7

Production of pHS using PDC2 Cell-Free Extract and Bioproduced pHCA-Containing Fermentation Medium in a Biphasic Reaction Medium The purpose of this Example was to demonstrate the production of pHS using PDC2 cell-free extract and pHCA, contained in a fermentation medium, using a biphasic reaction medium. The pHCA was first produced by fermentation using a recombinant strain of E. coli. The pHCA was then converted to pHS in a biphasic reaction medium, consisting of fermentation supernatant and toluene, using PDC2 cell-free extract.

The bioproduction of pHCA was done as described in Example 6. A 1.0 L jacketed Wheaton CelStir® reactor was charged with 0.4 L of the fermentation supernatant, obtained from the pHCA fermentation, as described in Example 6. The fermentation supernatant contained pHCA (3.3 g/L), cinnamic acid (CA), phenylalanine, tyrosine (all produced by the recombinant E. coli cells), and salts at pH 6.0. The buffering capacity and pHCA concentration were increased by adding 0.4 L of 25 g/L pHCA in 0.2 M sodium phosphate, pH 6.0 buffer. The final pHCA concentration was about 14.15 g/L. Cell-free extract containing PDC2 (0.20 mL, 36 Units; 2.02 mg protein), prepared as described in Example 1, was added along with 0.20 L of reagent grade toluene containing 5 mg of ProStab® 5415 (Ciba Specialty Chemicals, Tarrytown, N.Y.), as a polymerization inhibitor. The reactor was capped, placed on a magnetic stir plate and stirred at moderate speed. The reaction temperature was set at 33° C. The reaction was allowed to proceed for 15 h before terminating. The contents of the reactor were transferred to a 500 mL separatory funnel and the layers were allowed to separate. The organic layer (upper layer) contained an emulsion, which was broken by filtering through a glass-fritted Buchner funnel of medium porosity. The filtrate had two immiscible layers, a colorless organic layer and a yellow aqueous layer. The layers were separated by passing through phase-separated cellulose filter paper, which allowed the organic layer to selectively pass through into the receiving flask. The organic layer was dried over anhydrous magnesium sulfate, filtered and the toluene was removed by rotary evaporation. The pHS was isolated as described in Example 6 to yield 4.5 g of a crude off-white crystalline residue. The solid was recrystallized from and washed with hexane and dried under vacuum (60 mm Hg) to constant dryness to yield 2.87 g of a fine white crystalline product with a $^1$H-NMR spectrum identical to that of the pHS standard. The overall yield of this reaction was 1421 g pHS produced per g of cell-free catalyst. This Example demonstrates the high productivity achieved by PDC2 decarboxylase in the presence of crude fermentation components and a small quantity of polymerization inhibitor.

Example 8

Production of PHS in a Biphasic Reaction Medium using PDC2 Cell-Free Extract Immobilized on Oxirane Acrylic Beads The purpose of this Example was to demonstrate the production of pHS in a biphasic reaction medium, consisting of aqueous buffer and toluene, using PDC2 cell-free extract immobilized on oxirane acrylic beads.

Immobilization of Cell-Free Extract Using Oxirane Acrylic Beads

A glass scintillation vial was charged with 100 mg of oxirane acrylic beads (Sigma, CAS# 93356-75-3; 150 microns, macroporous; activation 800 µmol/g) and 8 mL 50 mM sodium phosphate, pH 6.0 buffer. The PDC2 cell-free extract (0.100 mL, 0.59 mg protein, 15 U), prepared as described in Example 1, was added and the contents were allowed to gently rock on a shaker overnight at ambient temperature. The mixture was centrifuged and then the supernatant was decanted. To treat unreacted epoxide sites on the beads, the beads were resuspended in 10 mL of 50 mM sodium phosphate buffer, pH 6.0, containing 0.83 M ethanolamine for 2 h at ambient temperature. The beads were washed three times with 10 mL portions of 50 mM sodium phosphate, pH 6.0 buffer and stored at ambient temperature in 0.2 M sodium phosphate, pH 6.0 buffer until use.

Production of pHS Using the Immobilized Cell-Free Extract

A glass vessel (containing an overhead stirrer with Teflon® and glass components) was charged with 5 mL of 30 mM PHCA in 0.2 M sodium phosphate, pH 6.0. The PDC2-oxirane acrylic beads (40 mg) and 3 mL of toluene were added to the vessel. The contents were stirred at room temperature. The progress of the decarboxylation reaction was monitored by TLC to assess the reaction progress. After 8 h, there was a single spot on the TLC plate and this spot had an $R_f$ value that corresponded to pHS. No attempts were made to recover the pHS from the toluene solution. This Example demonstrates pHS production using oxirane bead-immobilized PDC2 decarboxylase in a biphasic reaction medium.

Example 9

Prophetic Example of the Derivatization of Para-hydroxystyrene Prepared in a Biphasic Reaction Medium using PDC2 Cell-Free Extract The purpose of this prophetic Example is to demonstrate the chemical derivatization of pHS in the organic extractant from the biphasic reaction medium to form the derivatized compound para-acetoxystyrene. The pHCA is first produced by fermentation using a recombinant strain of *E. coli*. The bio-produced pHCA is then converted to pHS in a biphasic reaction medium, consisting of fermentation supernatant and toluene, using PDC2 cell-free extract. After the toluene layer is separated from the pHCA-depleted fermentation supernatant, the bio-produced pHS is reacted with acetic anhydride to form para-acetoxystyrene.

Bioproduction of pHCA

The bioproduction of PHCA is done as described in Example 6.

Production of pHS by Biocatalysis of Bio-produced PHCA

A 1.0 L jacketed Wheaton CelStir® reactor is charged with 0.335 L of the fermentation supernatant, obtained from a PHCA fermentation, as described in Example 6. The fermentation supernatant contains PHCA, cinnamic acid (CA), phenylalanine, tyrosine (all produced by the recombinant *E. coli* cells), and salts at pH 6.0. The pH of the pHCA-containing fermentation supernatant is adjusted to pH 6.0 using concentrated sulfuric acid for the enzymatic decarboxylation. Cell-free extract containing PDC2 (0.30 mL, 55 Units; 2.2 mg protein), prepared as described in Example 1, is added along with 0.15 L of reagent grade toluene containing 42 mg of ProStab® 5415 (Ciba Specialty Chemicals, Tarrytown, N.Y.), as a polymerization inhibitor. The reactor is capped, placed on a magnetic stir plate, and stirred at moderate speed. The reaction temperature is set at 40° C. The reaction is allowed to proceed for 2 h before terminating. The contents of the reactor are transferred to a 500 mL separatory funnel and the layers are allowed to separate. If the organic layer contains an emulsion, it is broken by filtering through a glass-fritted Buchner funnel of medium porosity. The filtrate has two immiscible layers, a colorless organic layer and a yellow aqueous layer. The layers are separated by passing through phase-separated cellulose filter paper, which allows the organic layer to selectively pass through into the receiving flask. The organic layer is recovered and immediately transferred to a 250 mL round-bottomed flask containing a stir bar. The flask is charged with pyridine (CAS110-86-1, 0.300 mL, 3.71 mmol) and acetic anhydride (CAS108-24-7, 4.0 mL, 42.4 mmol). The progress of the acetylation reaction is monitored by TLC until all of the pHS is converted and only a single spot appears on the TLC plate. A yellow oil is recovered by rotary evaporation under vacuum (13.3 kPa) with mild heating (30° C.). The isolated oil (1.41 g) is characterized by gas chromatography. Further purification of the acetoxystyrene product could be achieved by known methods (see for example Chosnek et. al. U.S. Pat. No. 5,136,083). This prophetic Example demonstrates how the pHS extracted into the organic medium of the biphasic reaction mixture may be derivatized to give a derivatized product such as para-acetoxystyrene.

What is claimed is:

1. A process for producing a derivatized compound of para-hydroxystyrene comprising:
   a) providing an enzyme source having para-hydroxycinnamic acid decarboxylase activity, wherein the enzyme source comprises a polypeptide having the amino acid sequence as set forth in SEQ ID NO:4, and wherein the enzyme source is selected from the group consisting of cell-free extract, partially purified enzyme, and purified enzyme;
   b) contacting the enzyme source with para-hydroxycinnamic acid in a biphasic reaction medium comprising an aqueous phase and an extractant, wherein the extractant is a water-immiscible organic solvent selected from the group consisting of toluene, methyl decanoate, 2-undecanone, dichloromethane, hexane, 2-decanol, 4-decanol, 3-decanone, 4-decanone, 1-nonanol, 2-nonanol, 2-heptanol and mixtures thereof, to form para-hydroxystyrene which is extracted into the extractant of the biphasic reaction medium;
   c) separating the extractant containing the para-hydroxystyrene after step b) from the aqueous phase; and
   d) chemically derivatizing the extractant containing the para-hydroxystyrene after step c) to form a derivatized compound of para-hydroxystyrene.

2. A process according to claim 1 wherein the derivatized compound is defined by the general formula:

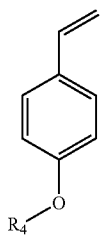

wherein R4 is selected from the group consisting of: methyl, t-butyl, alkyl, silyl ethers, allyl, t-butoxy carbonyl, hydroxyethoxy, acetoxy, formate, glycidyl, benzoate, phenylcarbonate, tetrahydropyran, benzyl, and poly(ethylene oxide).

3. A process according to claim 2 wherein the derivatized compound is para-acetoxystyrene.

4. A process for producing para-hydroxystyrene comprising:
   a) providing a production host which produces para-hydroxycinnamic acid;
   b) growing the production host in a fermentation medium wherein the production host produces para-hydroxycinnamic acid into the fermentation medium;
   c) contacting the fermentation medium from step (b) with an enzyme source having para-hydroxycinnamic acid decarboxylase activity, wherein the enzyme source comprises a polypeptide having the amino acid sequence as set forth in SEQ ID NO:4 and the enzyme source is selected from the group consisting of cell-free extract, partially purified enzyme, and purified enzyme, in a biphasic reaction medium comprising the fermentation medium and an extractant, and wherein the extractant is a water-immiscible organic solvent selected from the group consisting of toluene, methyl decanoate, 2-undecanone, dichloromethane, hexane, 2-decanol, 4-decanol, 3-decanone, 4-decanone, 1-nonanol, 2-nonanol, 2-heptanol and mixtures thereof, to form para-hydroxystyrene which is extracted into the extractant of the biphasic reaction medium;
   d) separating the extractant containing the para-hydroxystyrene after step c) from the fermentation medium; and
   e) optionally recovering the para-hydroxystyrene from the extractant.

5. A process according to claim 4 wherein the production host and insoluble materials are removed from the fermentation medium prior to the contacting of step (c).

6. A process according to claim 5 wherein the production host and insoluble materials are removed from the fermentation medium by filtration or centrifugation.

7. A process according to claim 4 wherein the production host is selected from the group consisting of *Escherichia*, *Methylosinus*, *Methylomonas*, *Pseudomonas*, *Streptomyces*, *Corynebacterium*, and *Rhodobacter*.

8. A process according to claim 4 wherein the enzyme source is immobilized.

9. A process according to claim 4 wherein the extractant is present in the biphasic reaction medium in an amount from about 5% to about 70% by volume.

10. A process according to claim 4 wherein the extractant is present in the biphasic reaction medium in an amount from about 20% to about 50% by volume.

11. A process according to claim 4 wherein the extractant is separated from the fermentation medium by use of a gravity settler, a centrifuge, or a hydrocyclone.

12. A process according to claim 4 wherein the enzyme source is recovered from the fermentation medium after the separating of step (d) for reuse.

13. A process according to claim 12 wherein the enzyme source is recovered from the fermentation medium using a method selected from the group consisting of filtration, ultrafiltration, nanofiltration, and centrifugation.

14. A process according to claim 4 wherein the recovering of step (e) is accomplished by means selected from the group consisting of evaporation, distillation, adsorption by resins, and adsorption by molecular sieves.

15. A process according to claim 4 wherein after step (e), the extractant is optionally added back to the biphasic reaction medium.

16. A process according to claim 4 wherein the fermentation medium after step (d) is optionally added back to the biphasic reaction medium.

17. A process for producing a derivatized compound of para-hydroxystyrene comprising:
   a) providing a production host which produces para-hydroxycinnamic acid;
   b) growing the production host in a fermentation medium wherein the production host produces para-hydroxycinnamic acid into the fermentation medium;
   c) contacting the fermentation medium from step (b) with an enzyme source having para-hydroxycinnamic acid decarboxylase activity, wherein the enzyme source comprises a polypeptide having the amino acid sequence as set forth in SEQ ID NO:4 and the enzyme source is selected from the group consisting of cell-free extract, partially purified enzyme, and purified enzyme, in a biphasic reaction medium comprising the fermentation medium and an extractant, wherein the extractant is a water-immiscible organic solvent selected from the group consisting of toluene, methyl decanoate, 2-undecanone, dichloromethane, hexane, 2-decanol, 4-decanol, 3-decanone, 4-decanone, 1-nonanol, 2-nonanol, 2-heptanol and mixtures thereof, to form para-hydroxystyrene which is extracted into the extractant of the biphasic reaction medium;

d) separating the extractant containing the para-hydroxystyrene after step c) from the fermentation medium; and e) chemically derivatizing the para-hydroxystyrene and the extractant after step d) to form a derivatized compound of para-hydroxystyrene.

18. A process according to claim 17 wherein the derivatized compound is para-acetoxystyrene.

* * * * *

SEQUENCE LISTING

```
<160> NUMBER OF SEQ ID NOS: 14

<210> SEQ ID NO 1
<211> LENGTH: 535
<212> TYPE: DNA
<213> ORGANISM: Lactobacillus plantarum

<400> SEQUENCE: 1
atgacaaaaa cttttaaaac acttgatgac tttctcggca cacactttat ctacacttat      60
gataacggct gggaatacga gtggtacgcc aagaacgacc acaccgttga ttaccgaatc     120
cacggtggga tggttgccgg tcgttgggtc actgatcaaa aagctgacat cgtcatgttg     180
accgaaggca tttacaaaat ttcttggact gaaccaactg ggactgacgt tgcactagac     240
ttcatgccca atgagaagaa actacacggt acgattttct tcccaaagtg ggttgaagaa     300
caccctgaaa ttacggtcac ttaccaaaac gaacacatcg atttaatgga acagtctcgt     360
gaaaagtatg ccacttatcc aaaactagtt gtacccgaat tgccaatat tacttacatg      420 ggcgagggcc aaaacaatga agatgtaatc agtgaagcac cttacaaaga aatgccgaat     480
```
gatattcgca acggcaagta cttgatcaaa actaccatcg tttaaataag taatg    535

<210> SEQ ID NO 2
<211> LENGTH: 174
<212> TYPE: PRT
<213> ORGANISM: Lactobacillus plantarum

<400> SEQUENCE: 2

Met Thr Lys Thr Phe Lys Thr Leu Asp Asp Phe Leu Gly Thr His Phe
1               5                   10                  15

Ile Tyr Thr Tyr Asp Asn Gly Trp Glu Tyr Glu Trp Tyr Ala Lys Asn
            20                  25                  30

Asp His Thr Val Asp Tyr Arg Ile His Gly Gly Met Val Ala Gly Arg
        35                  40                  45

Trp Val Thr Asp Gln Lys Ala Asp Ile Val Met Leu Thr Glu Gly Ile
    50                  55                  60

Tyr Lys Ile Ser Trp Thr Glu Pro Thr Gly Thr Asp Val Ala Leu Asp
65                  70                  75                  80

Phe Met Pro Asn Glu Lys Lys Leu His Gly Thr Ile Phe Phe Pro Lys
                85                  90                  95

Trp Val Glu Glu His Pro Glu Ile Thr Val Thr Tyr Gln Asn Glu His
            100                 105                 110

Ile Asp Leu Met Glu Gln Ser Arg Glu Lys Tyr Ala Thr Tyr Pro Lys
        115                 120                 125

Leu Val Val Pro Glu Phe Ala Asn Ile Thr Tyr Met Gly Glu Gly Gln
    130                 135                 140

Asn Asn Glu Asp Val Ile Ser Glu Ala Pro Tyr Lys Glu Met Pro Asn
145                 150                 155                 160

Asp Ile Arg Asn Gly Lys Tyr Leu Ile Lys Thr Thr Ile Val
                165                 170

<210> SEQ ID NO 3
<211> LENGTH: 486
<212> TYPE: DNA
<213> ORGANISM: Bacillus subtilis

<400> SEQUENCE: 3
atggaaaact ttatcggaag ccacatgatt tatacgtatg aaaacggatg ggaatacgag    60
atttatatta aaaacgacca tacaattgat tatagaattc atagcggaat ggttgccgga   120
cgctgggttc gagatcagga agtgaatatt gtcaaactga cagaaggcgt atataaagtg   180
tcttggacag agccgactgg cacggatgtt tcattaaact ttatgccaaa tgaaaaacgc   240
atgcatggca tttttcttc ccgaaatgg gtgcatgaac atcctgaaat tacggtttgc   300
taccaaaatg accacattga tttgatgaaa gaatcccgcg aaaaatatga aacgtatcca   360
aaatacgttg tacctgaatt tgcggaaatt acatttctga aaaatgaagg agtcgacaac   420
gaagaagtga tttcgaaggc tccttatgag ggaatgacag acgatattcg cgcgggaaga   480
ttataa   486

<210> SEQ ID NO 4
<211> LENGTH: 161
<212> TYPE: PRT
<213> ORGANISM: Bacillus subtilis

<400> SEQUENCE: 4

Met Glu Asn Phe Ile Gly Ser His Met Ile Tyr Thr Tyr Glu Asn Gly
1               5                   10                  15

-continued

```
Trp Glu Tyr Glu Ile Tyr Ile Lys Asn Asp His Thr Ile Asp Tyr Arg
             20                  25                  30

Ile His Ser Gly Met Val Ala Gly Arg Trp Val Arg Asp Gln Glu Val
         35                  40                  45

Asn Ile Val Lys Leu Thr Glu Gly Val Tyr Lys Val Ser Trp Thr Glu
     50                  55                  60

Pro Thr Gly Thr Asp Val Ser Leu Asn Phe Met Pro Asn Glu Lys Arg
 65                  70                  75                  80

Met His Gly Ile Ile Phe Phe Pro Lys Trp Val His Glu His Pro Glu
                 85                  90                  95

Ile Thr Val Cys Tyr Gln Asn Asp His Ile Asp Leu Met Lys Glu Ser
            100                 105                 110

Arg Glu Lys Tyr Glu Thr Tyr Pro Lys Tyr Val Val Pro Glu Phe Ala
        115                 120                 125

Glu Ile Thr Phe Leu Lys Asn Glu Gly Val Asp Asn Glu Glu Val Ile
    130                 135                 140

Ser Lys Ala Pro Tyr Glu Gly Met Thr Asp Asp Ile Arg Ala Gly Arg
145                 150                 155                 160

Leu
```

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
ggtaattcat atgacaaa                                                  18

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tcacgtgaaa cattacttat t                                              21

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
gtgtgtcata tggaaaact                                                 19

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
tcgcgggaat tgtgatggt                                                 19

```
<210> SEQ ID NO 9
<211> LENGTH: 66
<212> TYPE: DNA
<213> ORGANISM: Artificial Sequence
<220> FEATURE:
<223> OTHER INFORMATION: Primer

<400> SEQUENCE: 9
aattcatcag gatctgaacg ggcagctgac ggctcgcgtg gcttaacgtc ttgagcgatt      60
gtgtag                                                                66

<210> SEQ ID NO 10
<211> LENGTH: 64
<212> TYPE: DNA
<213> ORGANISM: Artificial Sequence
<220> FEATURE:
<223> OTHER INFORMATION: Primer

<400> SEQUENCE: 10
aaaacattat ccagaacggg agtgcgcctt gagcgacacg aatatgaata tcctccttag      60
ttcc                                                                  64

<210> SEQ ID NO 11
<211> LENGTH: 40
<212> TYPE: DNA
<213> ORGANISM: Artificial Sequence
<220> FEATURE:
<223> OTHER INFORMATION: Primer

<400> SEQUENCE: 11
ctaaggagga tattcatatt cgtgtcgctc aaggcgcact                            40

<210> SEQ ID NO 12
<211> LENGTH: 66
<212> TYPE: DNA
<213> ORGANISM: Artificial Sequence
<220> FEATURE:
<223> OTHER INFORMATION: Primer

<400> SEQUENCE: 12
cgacttcatc aatttgatcg cgtaatgcgg tcaattcagc aaccatggtc tgtttcctgt      60
gtgaaa                                                                66

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
caaccgcgca gtgaaatgaa atacgg                                          26

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
gcgctccgga acataaatag gcagtc                                          26
```